US009449219B2

(12) United States Patent
Bilet et al.

(10) Patent No.: US 9,449,219 B2
(45) Date of Patent: Sep. 20, 2016

(54) SYSTEM AND METHOD FOR ACTIVITY MONITORING

(71) Applicant: Elwha LLC, Bellevue, WA (US)

(72) Inventors: Maxime Jean Jerome Bilet, Bellevue, WA (US); Roderick A. Hyde, Redmond, WA (US); Muriel Y. Ishikawa, Livermore, CA (US); Jordin T. Kare, Seattle, WA (US); Nathan P. Myhrvold, Bellevue, WA (US); Tony S. Pan, Cambridge, MA (US); Nels R. Peterson, Bellevue, WA (US); Clarence T. Tegreene, Mercer Island, WA (US); Lowell L. Wood, Jr., Bellevue, WA (US); Victoria Y. H. Wood, Livermore, CA (US); Christopher Charles Young, Seattle, WA (US)

(73) Assignee: ELWHA LLC, Bellevue, WA (US)

( * ) Notice: Subject to any disclaimer, the term of this patent is extended or adjusted under 35 U.S.C. 154(b) by 550 days.

(21) Appl. No.: 13/777,548

(22) Filed: Feb. 26, 2013

(65) Prior Publication Data
US 2014/0244344 A1    Aug. 28, 2014

(51) Int. Cl.
| *G06K 9/00* | (2006.01) |
| *G06F 19/00* | (2011.01) |
| *G06F 3/01* | (2006.01) |
| *G06F 3/033* | (2013.01) |
| *G06Q 10/06* | (2012.01) |
| *G06Q 50/12* | (2012.01) |

(52) U.S. Cl.
CPC ........... *G06K 9/00335* (2013.01); *G06F 3/017* (2013.01); *G06F 3/033* (2013.01); *G06F 19/00* (2013.01); *G06F 19/3475* (2013.01); *G06K 9/00624* (2013.01); *G06Q 10/0635* (2013.01); *G06Q 50/12* (2013.01)

(58) Field of Classification Search
None
See application file for complete search history.

(56) References Cited

U.S. PATENT DOCUMENTS

| 6,236,317 | B1 | 5/2001 | Cohen et al. | |
| 6,971,575 | B2* | 12/2005 | Tsikos et al. | 235/462.01 |
| 7,423,533 | B1 | 9/2008 | LeBlond et al. | |
| 8,512,139 | B2* | 8/2013 | Williams et al. | 463/32 |
| 8,594,814 | B2* | 11/2013 | Rovaglio et al. | 700/83 |
| 2001/0015123 | A1* | 8/2001 | Nishitani | A63B 71/0686 84/615 |
| 2001/0024512 | A1* | 9/2001 | Yoronka | G06K 9/00335 382/103 |
| 2005/0105772 | A1* | 5/2005 | Voronka | G06T 7/2033 382/103 |
| 2007/0229350 | A1* | 10/2007 | Scalisi et al. | 342/350 |
| 2010/0015585 | A1* | 1/2010 | Baker | A63B 24/0003 434/247 |
| 2010/0164728 | A1 | 7/2010 | Plost | |
| 2010/0317420 | A1* | 12/2010 | Hoffberg | 463/1 |
| 2010/0328443 | A1 | 12/2010 | Lynam et al. | |
| 2012/0038550 | A1* | 2/2012 | Lemmey | A63F 13/12 345/156 |
| 2012/0075464 | A1 | 3/2012 | Derenne et al. | |
| 2012/0124525 | A1* | 5/2012 | Kang | G06F 3/011 715/863 |
| 2012/0146792 | A1 | 6/2012 | De Luca et al. | |
| 2012/0154582 | A1* | 6/2012 | Johnson et al. | 348/143 |

(Continued)

*Primary Examiner* — Gurkanwaljit Singh

(57) ABSTRACT

A system for activity monitoring includes a tracking component, an activity identification component, a procedural component, and a notification component. The tracking component tracks an individual and one or more objects in a work area using a three-dimensional tracking system. The activity identification component identifies an activity of the individual and any of the one or more objects that are affected by the activity. The procedural component determines whether the activity violates one or more procedural rules pertaining to one or more of the individual, the work area, and the one or more objects. The notification component provides a notification of a violation.

39 Claims, 9 Drawing Sheets

(56) References Cited

U.S. PATENT DOCUMENTS

| | | | | |
|---|---|---|---|---|
| 2012/0172126 A1* | 7/2012 | Padovani | G06F 3/011 | |
| | | | 463/36 | |
| 2012/0190981 A1* | 7/2012 | Harris | A61B 19/2203 | |
| | | | 600/439 | |
| 2012/0212582 A1 | 8/2012 | Deutsch | | |
| 2012/0213436 A1* | 8/2012 | Grindstaff | G06T 5/008 | |
| | | | 382/167 | |
| 2012/0290950 A1* | 11/2012 | Rapaport et al. | 715/753 | |
| 2013/0278631 A1* | 10/2013 | Border et al. | 345/633 | |
| 2014/0126767 A1* | 5/2014 | Daon et al. | 382/103 | |

* cited by examiner

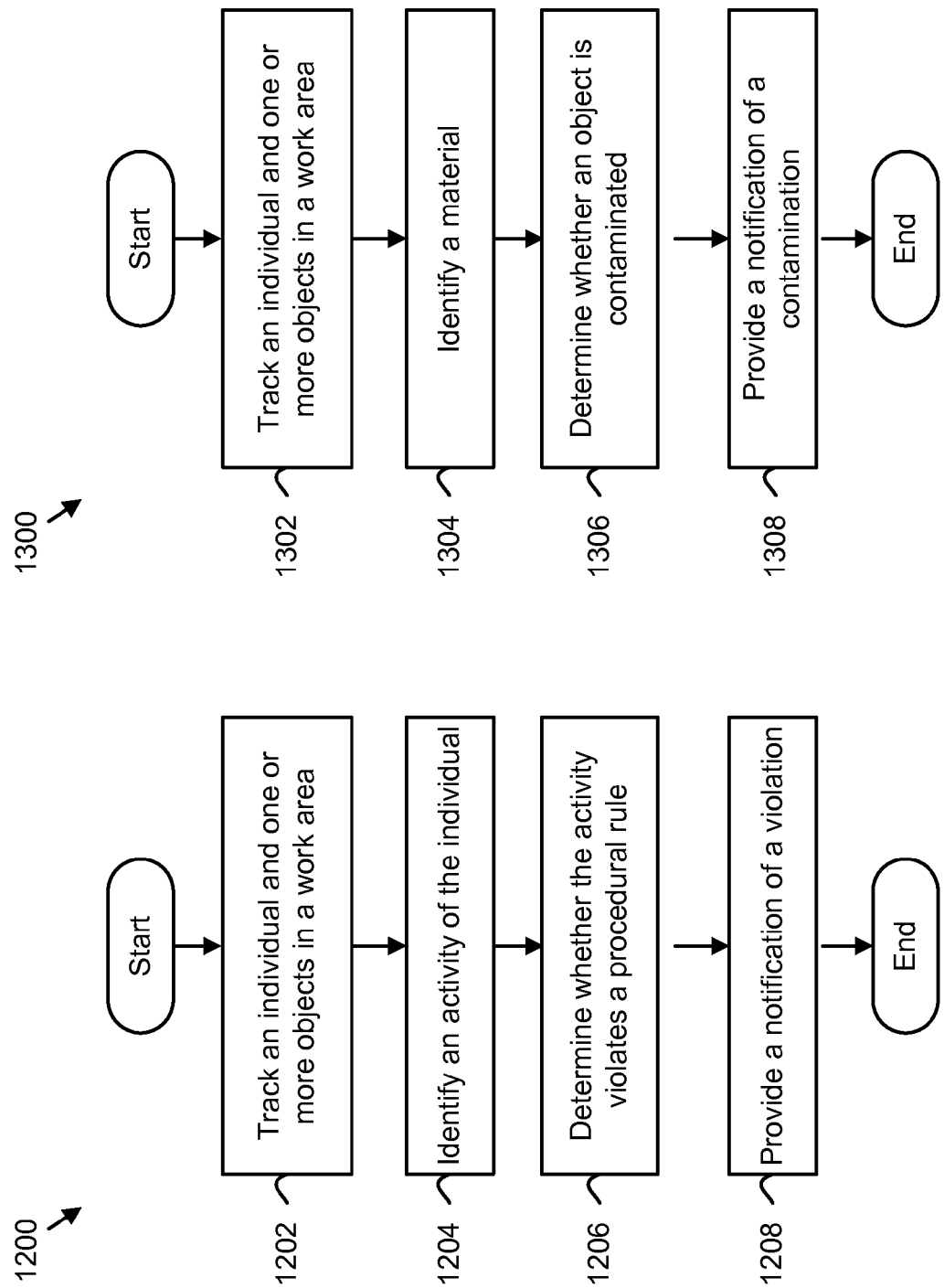

SYSTEM AND METHOD FOR ACTIVITY MONITORING

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.
Priority Applications:
  NONE
Related Applications:
  U.S. patent application Ser. No. 13/777,553, entitled SYSTEM AND METHOD FOR CONTAMINATION MONITORING, naming Maxime Jean Jerome Bilet, Roderick A. Hyde, Muriel Y. Ishikawa, Jordin T. Kare, Nathan P. Myhrvold, Tony S. Pan, Nels R. Peterson, Clarence T. Tegreene, Lowell L. Wood, Jr., Victoria Y. H. Wood, and Christopher Charles Young as inventors, filed Feb. 26, 2013.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

BRIEF DESCRIPTION OF THE FIGURES

FIG. 12 illustrates a flow chart of one embodiment of a method for activity monitoring.

FIG. 13 illustrates a flow chart of one embodiment of a method for contamination monitoring.

DETAILED DESCRIPTION

Figure 1:
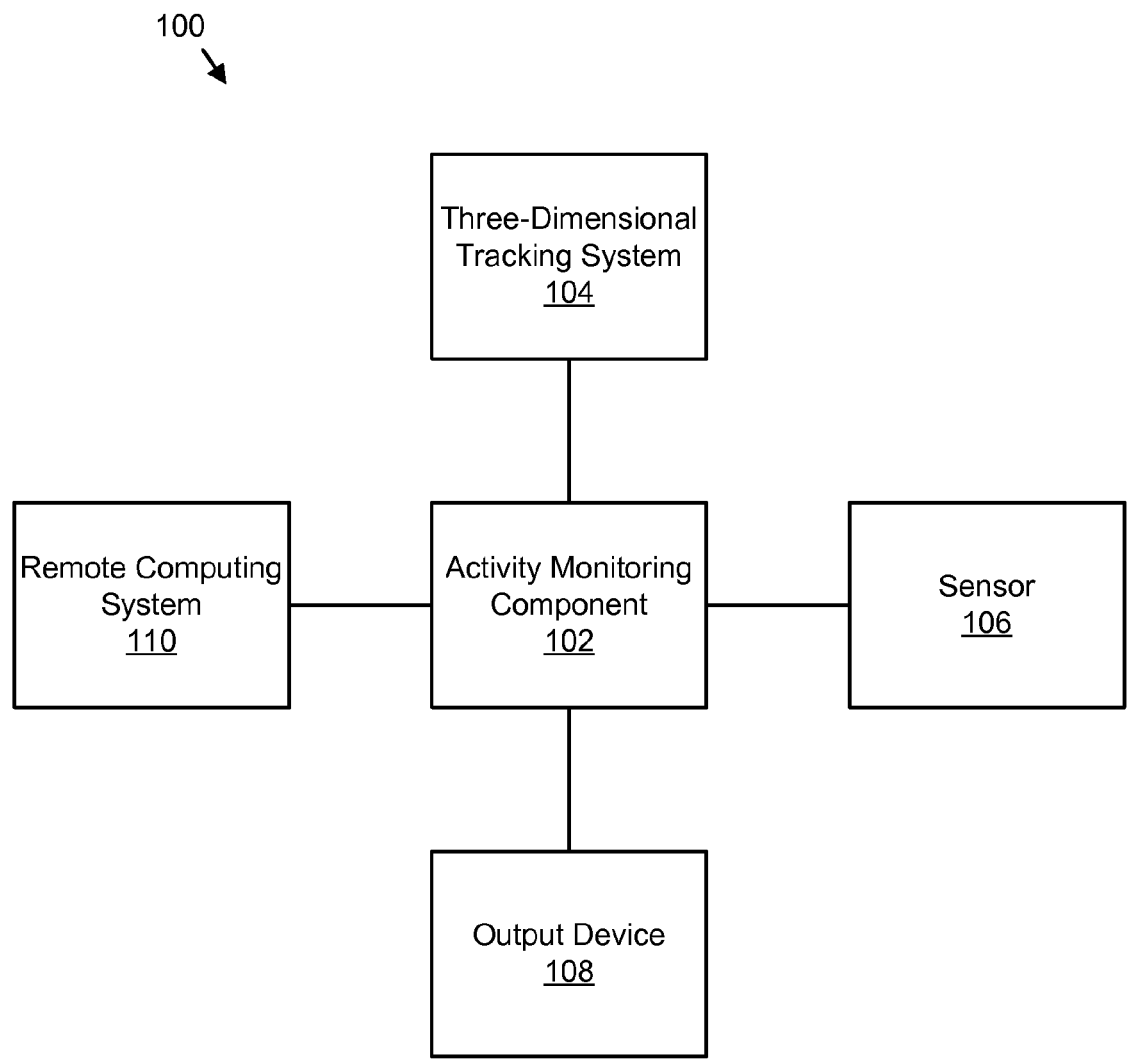
FIG. 1 is a schematic block diagram illustrating one embodiment of an activity monitoring system.

Food borne illness and disease can be dangerous and can cause serious sickness or death. In the case of contaminated restaurant food or mass produced food items, large numbers of people can be adversely affected. Generally, various food handling procedures, if followed, can reduce the chances of customers contracting these dangerous food borne illnesses and diseases. For example, simple procedures, such as hand washing, keeping raw meats or animal products separate from food items that are ready to be consumed, refrigerating perishables at proper temperatures, and cooking foods to a sufficient heat, can significantly reduce the risk that food items served to customers might cause illness.

These various rules and methods are generally well understood and followed by highly skilled chefs or other food preparers. However, high stress situations, multiple workers, poor kitchen layouts, or other situations can cause even the most experienced chefs to make mistakes. In the case of unskilled workers, failure to follow good kitchen rules can be due to lack of knowledge, bad habits, or even laziness. Thus, kitchens with unskilled workers often implement extremely tight procedures and processes such that the possibility for even unskilled workers to make mistakes is significantly reduced. However, even tightly designed procedures cannot prevent all mistakes. Thus, even though procedures to prevent food contamination are often known, lapses in complying with these procedures still take place. Because of the severity of potential consequences, such lapses in procedural compliance are not acceptable.

To encourage proper food handling, governments and employers often create various laws and rules requiring compliance with a variety of food handling procedures. However, compliance with these laws and rules are very difficult to enforce. In the case of legal requirements, compliance or noncompliance is generally determined based on inspections by government employees, tips from current or previous employees, or complaints from the general public. However, such methods of ensuring compliance often fail to capture how a kitchen or other food handling facility actually handles food and follows legal requirements on a day-to-day basis.

In view of the foregoing, Applicants have recognized that a need exists for work area activity monitoring to detect violation of procedural rules, contamination, or other potential problems. Applicants herein disclose methods and systems for monitoring activities of an individual in a work area. In one embodiment, a system for activity monitoring tracks an individual and one or more objects within a work area. The system identifies an activity of the individual and any of the objects affected by the activity. The system determines whether the activity violates a procedural rule and provides a notification of any violation.

The present disclosure provides examples and embodiments of activity and contamination monitoring within a kitchen environment. However, kitchens are only one example of a work area that may benefit from activity monitoring. Other work areas which may beneficially be monitored using the systems and methods herein include research laboratories, food packaging environments, food processing environments, product assembly environments, manufacturing environments, healthcare environments, or the like. For example, manufacturing or assembly facilities that process high-value items that could be damaged based on incorrect procedures, such as use of an incorrect tool, may violate regulations or damage products. Other example work areas to be monitored may include any work area where transitioning of items from one activity or area to another can result in contamination, infection, or the like. One of skill in the art will recognize other environments that have important procedural requirements which may benefit from activity or contamination monitoring and which fall within the scope of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 is a schematic diagram illustrating one embodiment of a activity monitoring system 100. The activity monitoring system 100 may also be referred to herein as a contamination monitoring system. The activity monitoring system 100 may be used to monitor an individual and one or more objects within a work area. The activity monitoring system 100 includes an activity monitoring component 102, a three-dimensional tracking system 104, a sensor 106, an output device 108, and a remote computing system 110.

The activity monitoring component 102 monitors activity or contamination within a work area. The monitoring may be used for training purposes, rule or legal compliance, food safety monitoring, or the like. The activity monitoring component 102 may monitor an individual and one or more objects in a work area based on input from the three-dimensional tracking system 104, sensor 106 and/or the remote computing system 110. The activity monitoring component 102 includes computer software and/or hardware to perform activity tracking, individual or object identification, and/or violation detection functions. The activity monitoring component 102 may provide output to the output device 108, remote computing system 110, or other component or system to provide notification of the occurrence of a violation or contamination. The activity monitoring component 102 will be discussed in greater detail in relation to FIG. 3.

A three-dimensional tracking system 104 obtains data about a work area and any individuals or objects in the work area. The three-dimensional tracking system 104 provides the data to the activity monitoring component 102 for tracking the individuals and/or objects. In one embodiment, the three-dimensional tracking system 104 includes a range imaging system. An example of a currently available range imaging system that may be used as three-dimensional tracking system 104 is the Microsoft® Kinect®. Other systems that use projection and detection ranging methods may also be used. According to one embodiment, any range imaging system or body tracking system capable of determining a position of an individual or one or more objects within a work area may be used.

The three-dimensional tracking system 104 may include one or more devices for observing a work area and determining locations of individuals or objects in the work area. In one embodiment, the three-dimensional tracking system 104 includes a range finder, such as a laser range finder, radar range finder, or other range finder for determining distances to objects or individuals in the work area.

The three-dimensional tracking system 104 may include one or more imaging devices. In one embodiment, the three-dimensional tracking system 104 includes one or more visible wave length cameras. In another embodiment, the three-dimensional tracking system 104 includes one or more infrared cameras. The cameras of the three-dimensional tracking system 104 may include still or video cameras. In one embodiment, three-dimensional information may be derived from stereo imaging devices that include two or more cameras having different points of view.

In one embodiment, the three-dimensional tracking system 104 includes a range finder and one or more cameras. The activity tracking system 100 may include a plurality of three-dimensional tracking systems 104 for providing more detailed coverage or to eliminate blind spots within the work area. Similarly, the cameras, range finders, or other devices of a three-dimensional tracking system 104 may be capable of panning to change a field of view and/or zooming in or out to increase detail or broaden a field of view. For example, the activity tracking system 100 may provide system-controlled pan and zoom to provide intermittent coverage to larger areas or detailed coverage to smaller areas.

The three-dimensional tracking system 104 may forward data obtained by a camera or range finder to the activity monitoring component 102 for processing. Alternatively, the three-dimensional tracking system 104 may be configured to process the data and determine locations and/or identify individuals and objects within the work area. The three-dimensional tracking system 104 may then forward the resulting location and/or identification information to the activity monitoring component 102.

A sensor 106 may include a variety of sensor types for tracking activity within a work area. In one embodiment, a plurality of sensors 106 may be used to obtain various types of data within the work area. Example sensor types include flow sensors, pressure sensors, identification tag sensors, temperature sensors, proximity sensor, and the like. The sensors 106 may be fixedly mounted within the work area or may be integrated into or mounted on an object or an individual. The information gathered by the sensors 106 may be provided to the activity monitoring component 102 for processing.

An output device 108 may provide output indicating that an activity has violated a rule, output that a contamination has occurred, or other information regarding activity within the work area. The output device 108 may include a display screen, an indicator light, a spotlight, a laser pointer, a speaker, or the like. In one embodiment, multiple output devices 108 may be included to provide notifications in a variety of different ways within or outside of a work area.

The remote computing system 110 may receive violation or contamination information from the activity monitoring component 102. The remote computing system 110 may be located at a remote location and may allow a government, company, or other organization to monitor a work area. In one embodiment, the remote computing system 110 may receive notifications regarding violating activities, food contaminations, legal violations, or other procedural problems. For example, the three-dimensional tracking system 104 and sensors 106 may be installed within a commercial kitchen and the activity monitoring component 102 may report violations to the remote computing system 110 operated by a government, company headquarters, or the like.

The remote computing system 110 may also monitor operation of the activity monitoring component 102. For example, the remote computing system may communicate periodically with the activity monitoring component 102 to ensure that it remains operational. Similarly, the remote computing system 110 may provide software updates or other information to the activity monitoring component 102.

In one embodiment, at least a portion of the activity monitoring system 100 is transportable for use at different locations. For example, the activity monitoring component 102, three-dimensional tracking system 104, sensor 106, and/or output device 108 may be transportable from one location to another to perform periodic inspections, periodic training, or the like. In one embodiment, temporary or permanent installation of the system 100 may be mandated in response to health violations or other violations.

The remote computing system 110 may also issue a citation based on procedural problems. The citation may be provided to the output device 108, or separately outside of the activity monitoring system 100, such as via mail.

Figure 2:
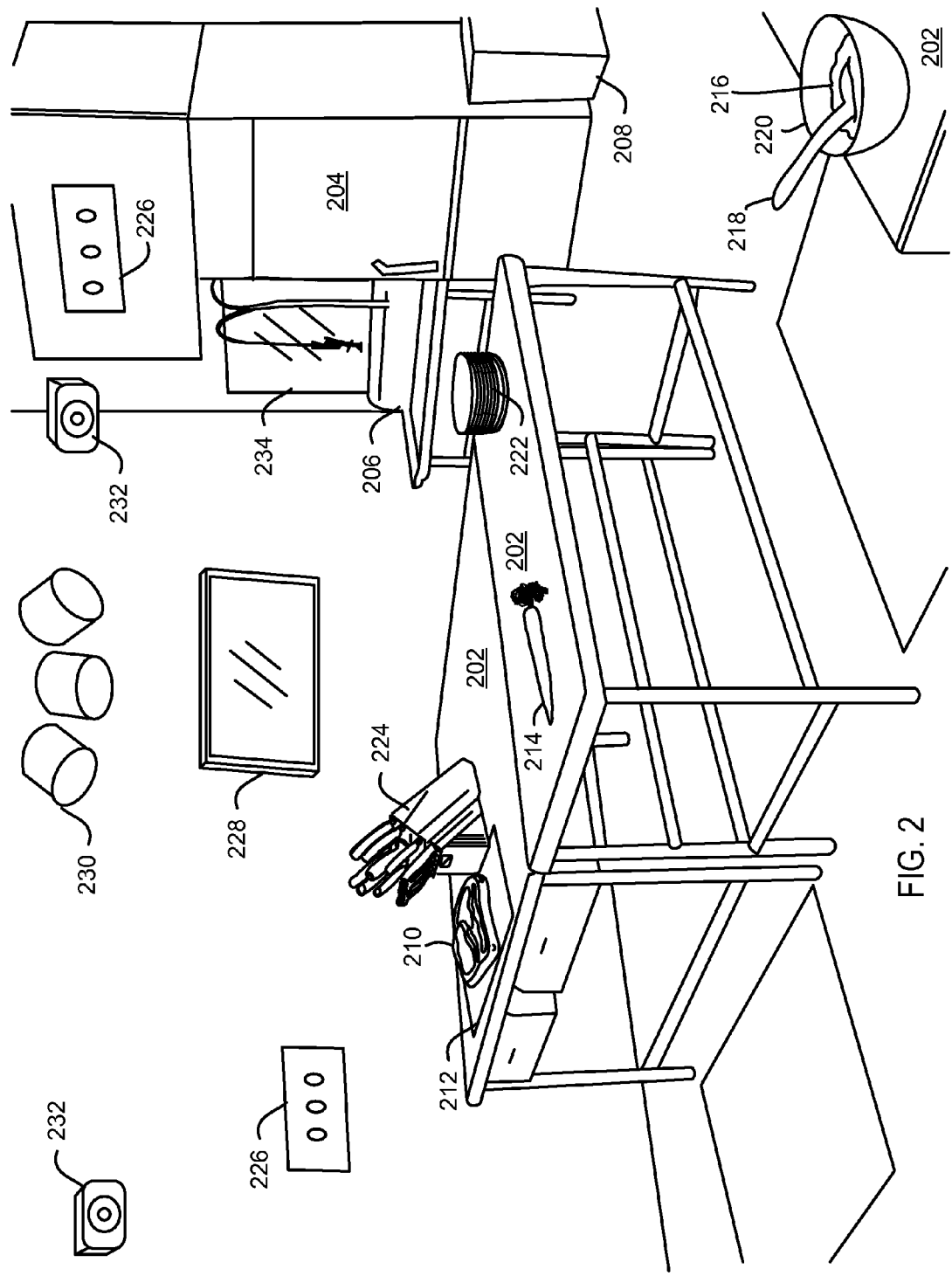
FIG. 2 is a perspective view illustrating one embodiment of a work area to be monitored.

FIG. 2 is a perspective view of an example kitchen work area. Examples of kitchen work areas may include commercial or non-commercial kitchens. The perspective view of FIG. 2 illustrates an example camera view that may be received by three-dimensional tracking system 104. The view illustrates example work area objects, food items, and other objects that may be monitored by an activity monitoring system 100. The kitchen work area includes a plurality of counter surfaces 202. The kitchen work area also includes a fridge 204 for storing food items or ingredients, a washbasin 206 for washing dishes and tableware, a waste receptacle 208, and the like. Also in the work area are a number of food items including a cut of meat 210 on a cutting board 212, a vegetable 214, and ingredients 216 with a mixing spoon 218 in a mixing bowl 220. Plates 222 and knife set 224, with a plurality of knives, are also shown.

Additionally, portions of an activity monitoring system 100 are shown. Face plates 226 of three-dimensional tracking systems 104 for observing the kitchen work area are mounted within the kitchen area. Example output devices 108 that include a display 228, spotlights 230, and speakers 232 are also shown. A number of sensors (not shown) may also be located within the kitchen work area or the objects of the kitchen work area to provide input for tracking activities. A mirror 234 may increase a field of view of a three-dimensional tracking system 104 to allow monitoring of an individual who is facing away from a three-dimensional tracking system 104 and towards the mirror 234.

Figure 3:
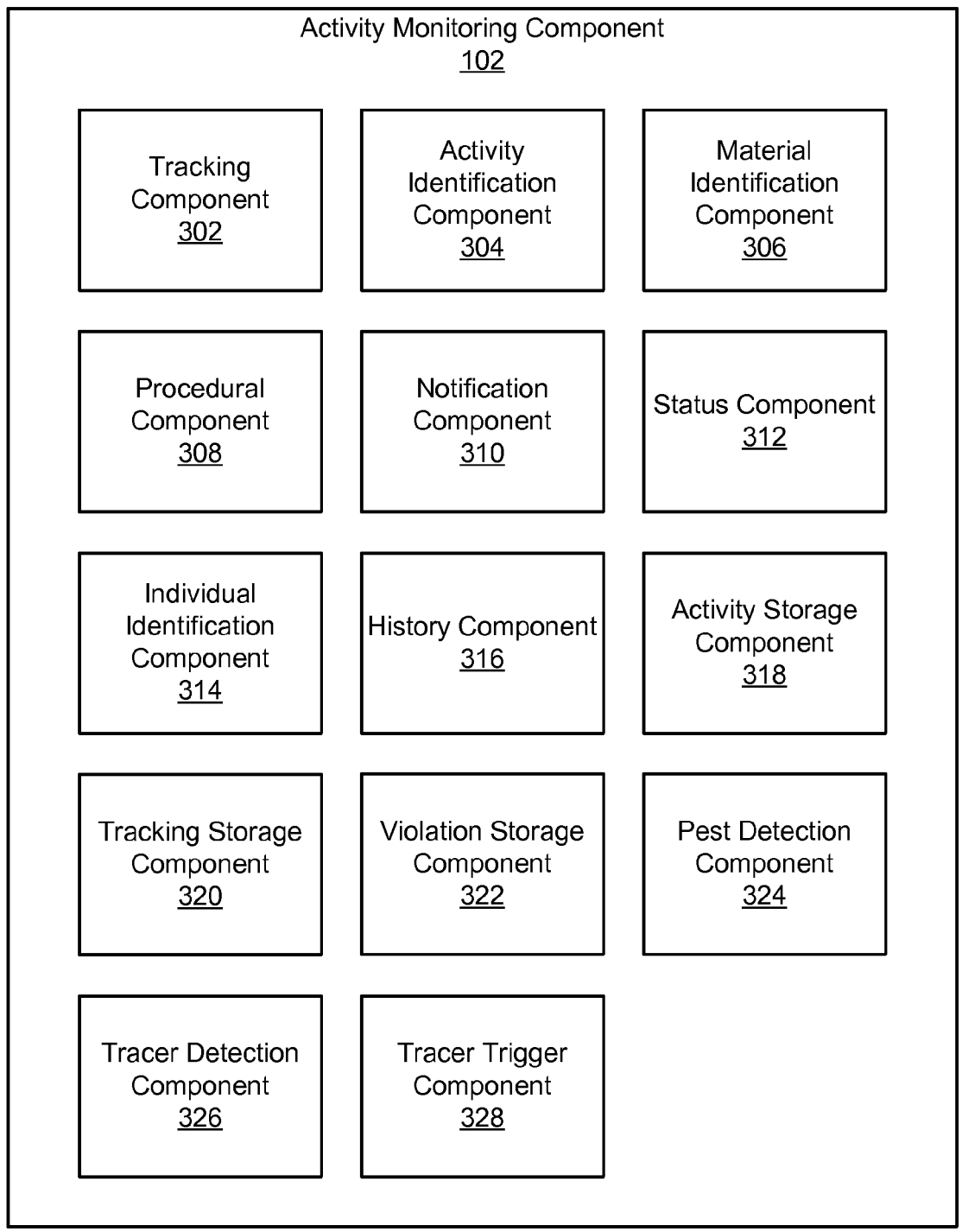
FIG. 3 is a schematic block diagram illustrating one embodiment of an activity monitoring component.

FIG. 3 is a schematic block diagram of an activity monitoring component 102. The activity monitoring component 102 includes a tracking component 302, an activity identification component 304, a material identification component 306, a procedural component 308, a notification component 310, a status component 312, an individual identification component 314, a history component 316, an activity storage component 318, a tracking storage component 320, a violation storage component 322, a pest detection component 324, a tracer detection component 326, and a tracer trigger component 328. The components 302-328 are given by way of example only and may not all be included in all embodiments. In fact, various embodiments may include only one or any combination of two or more of the components 302-328 without limitation.

The activity monitoring component 102 may include one or more hardware and/or software components for activity or contamination monitoring. In one embodiment, the activity monitoring component 102 may include code installed on a computing system and configured to be executed by a processor. In another embodiment, the components 302-328 of the activity monitoring component 102 may be implemented across two or more devices or computers. According to one embodiment, at least portions of one or more of the components 302-328 may be included within a three-dimensional tracking system 104, sensor 106, output device 108, or remote computing system 110.

The tracking component 302 tracks an individual and one or more objects in a work area. The tracking component 302 may track by storing or updating a location of an individual or object. In one embodiment, previous locations or movements may also be detected, stored, and/or provided to another module. In one embodiment, the tracking component 302 uses a three-dimensional tracking system 104. For example, the tracking component 302 may receive video information or range finding information from a camera or range finder of the three-dimensional tracking system 104. In one embodiment, the tracking component 302 may receive location information from the three-dimensional tracking system 104 and use that information to track a current and/or previous location of the individual. In another embodiment, the tracking component 302 may receive video footage information, image information, or range finding information and process the information to determine a location of the individual or object. For example, the tracking component 302 may receive a video of the work area illustrated in FIG. 2 and process the video feed to track the location of one or more objects and an individual.

The tracking component 302 tracks a location of an individual within a work area. For example, as an individual moves about the kitchen work area of FIG. 2, the tracking component 302 may track the individual's location. In one embodiment, the tracking component 302 tracks the location of the individual in relation to one or more of the work area objects, such as the counter surfaces 202, a floor, a sink or washbasin 206, a stovetop, an oven, a grill, a waste receptacle 208, a food storage location or container, or the like. For example, other types of work area objects may be encountered in types of work areas other than kitchens. In one embodiment, the tracking component 302 tracks the location of the individual in relation to logical areas in the work area. The tracking component 302 may track specific portions of the individual's body, such as where an individual puts his or her hands.

Figure 4:
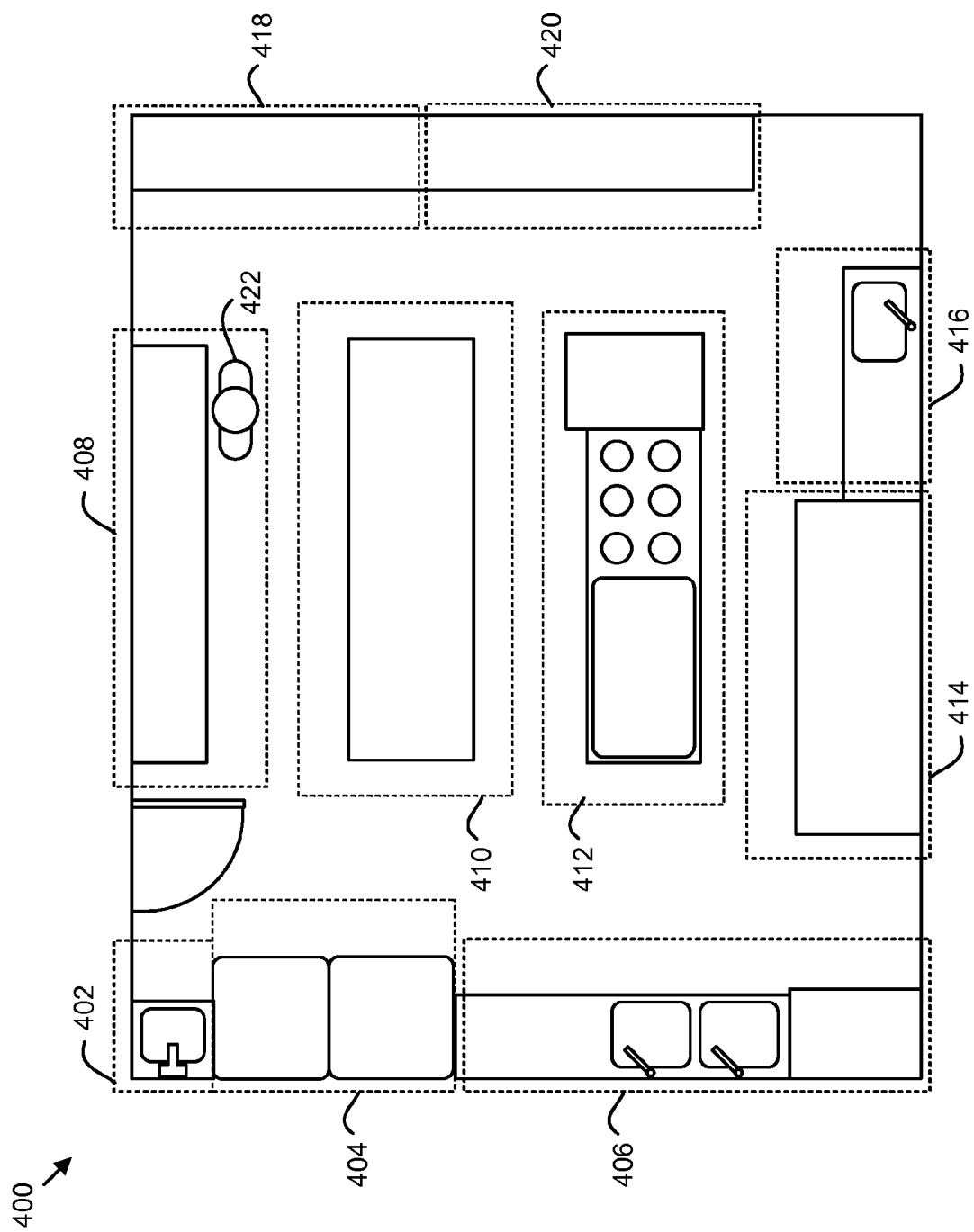
FIG. 4 is a plan view illustrating one embodiment of logical areas in a work area.

FIG. 4 illustrates a top view of a kitchen work area 400 that has been divided into a plurality of logical areas. A hand washing area 402 includes a sink and faucet for hand washing. A cold storage area 404 includes fridges for storing perishable food items. A dish washing area 406 includes a dishwasher, sinks, and counter space for washing dishes. A first foodstuff preparation area 408 includes counter space for preparing food or food orders. A raw meat area 410 includes counter space for preparing raw meats, raw animal products, or other food items that need to be cooked prior to serving or have a danger of harboring food borne illness or disease. A cooking area 412 includes a grill, a stove, and an oven for cooking food. A storage area 414 includes cabinets and drawers for storing food items, ingredients, and/or dishes. A foodstuff washing area 416 includes a sink and counter space to wash food items. A pass through 418 provides a sanitary counter space for passing prepared plates or other food orders to servers, customers, or the like. A second foodstuff preparation area 420 provides another counter space for preparing food items or food orders. An individual 422 is also shown within the kitchen work area 400. The logical areas 402-420 are examples only. Additional example areas which may be present in some work areas include a foodstuff reception area, a supply reception area, a sample reception area, an object unpacking area, a tool washing area, an allergen free area, a sterile area, or the like.

According to one embodiment, as the individual 422 moves about the kitchen work area 400, the tracking component 302 tracks the location of the individual 422 within the logical areas 402-420. For example, the tracking component 302 may determine that the individual is within the first foodstuff preparation area 408 and may track the individual 422 as the individual 422 moves to or through another logical area. Similarly, the location of one or more objects may be tracked as they are moved between different logical areas 402-420.

The tracking component 302 also tracks one or more objects within the work area. The one or more objects may include any objects or materials within the work area, such as those depicted in FIGS. 2 and 4. Some examples of objects that may be tracked by the tracking component include a food item, tableware, food preparation equipment, laboratory equipment, laboratory samples, a tool, one or more parts to be assembled, a medical device, and a cleaning implement. Examples of tableware include items such as a utensil, a plate, a bowl, a cutting board, a knife, a mixing tool, a serving tool, and the like. One of skill in the art will recognize that different types of work areas may include different types of objects to be tracked.

The tracking component 302 may track a body position or gesture of the individual 422. For example, the tracking component 302 may track the location and/or a position of an appendage of the individual 422. The tracking component 302 tracks the location of the individual's appendages, such as arms, one or both hands, head, and/or legs. According to one embodiment, each appendage may be tracked separately and/or independently. For example, the tracking component 302 may track the location of one hand within a first logical area and the location of a second hand in a second logical area. Additionally or alternatively, the tracking component 302 may track a body position of the individual 422. In one embodiment, tracking the body position comprises tracking a portion of the body with respect to another portion of the body. For example, the tracking component 302 may track a location of one appendage in relation to another appendage or an angle formed between joints. The tracking component 302 may also track movement of a hand of the individual or an object.

Figure 5:
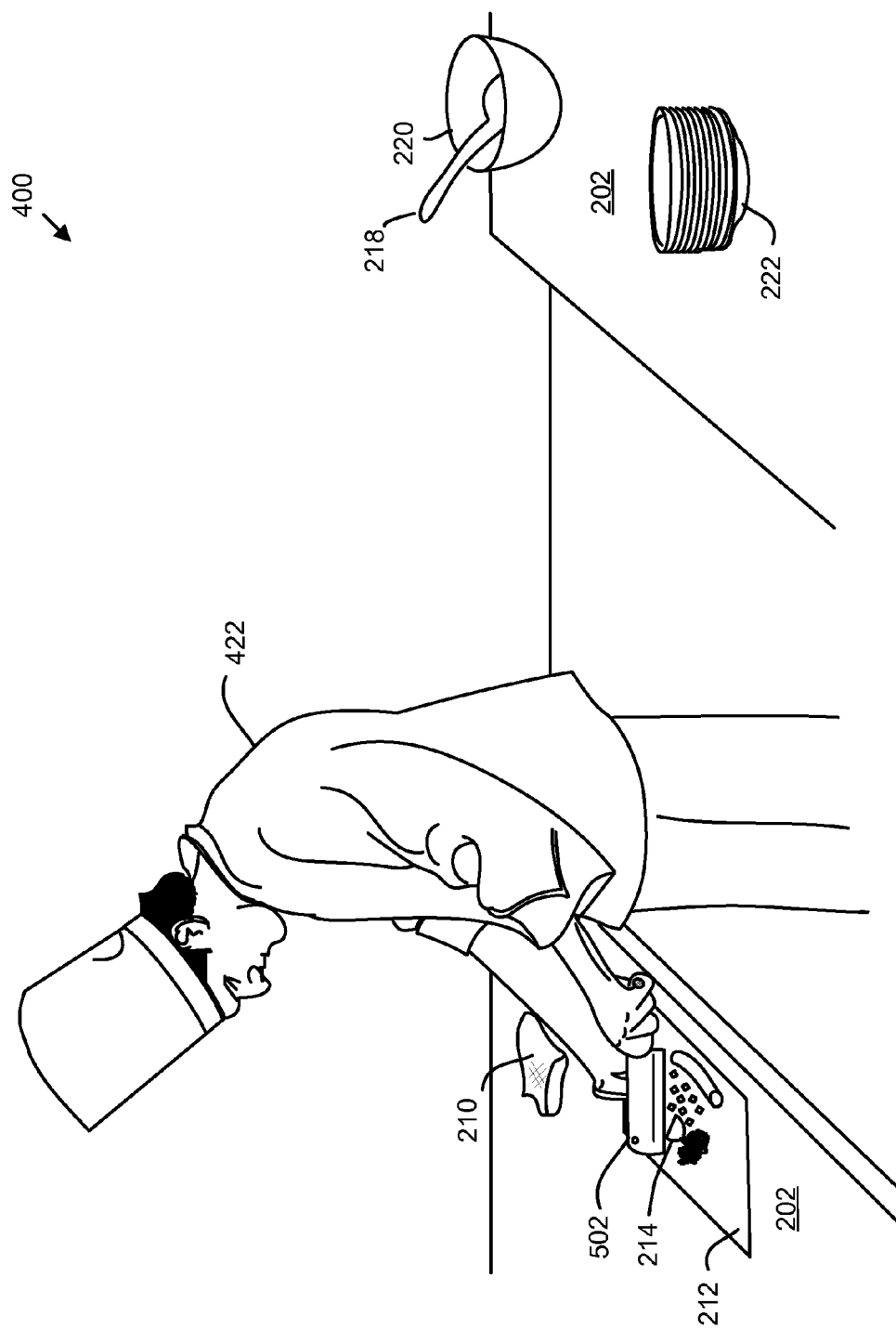
FIG. 5 is a perspective view illustrating an individual performing a chopping activity in a work area, according to one embodiment.

FIG. 5 illustrates a perspective view of an individual 422 within a kitchen work area 400. An individual, and counter surfaces 202 are displayed with a variety of objects resting thereon. The individual is located at one counter surface 202 chopping up a vegetable 214 on a cutting board 212 using a knife 502. A cut of meat 210 is also located on the counter surface near the cutting board 212. On the cutting surface 202 behind the individual 422 a mixing spoon 218 in a mixing bowl 220 and a number of plates 222 are shown.

According to one embodiment, the tracking component 302 may track the individual 422 within the work area 400. In one embodiment, the tracking component 302 will track the movement of the individual's hands as the individual cuts the vegetable 214 using the knife 502. The body position of the individual 422 will be tracked. For example, the tracking component 302 may track a location of the hands, arms, legs, back, head, and the like of the individual. Approximate angles between joints and relative positions may also be tracked. In one embodiment, estimates of positions may be determined based on an anatomical model of the individual or other software module. Thus, an anatomical or software model (such as used in the Microsoft® Kinect® may be used extrapolate motions or activities not directly "visible".

Figure 6:
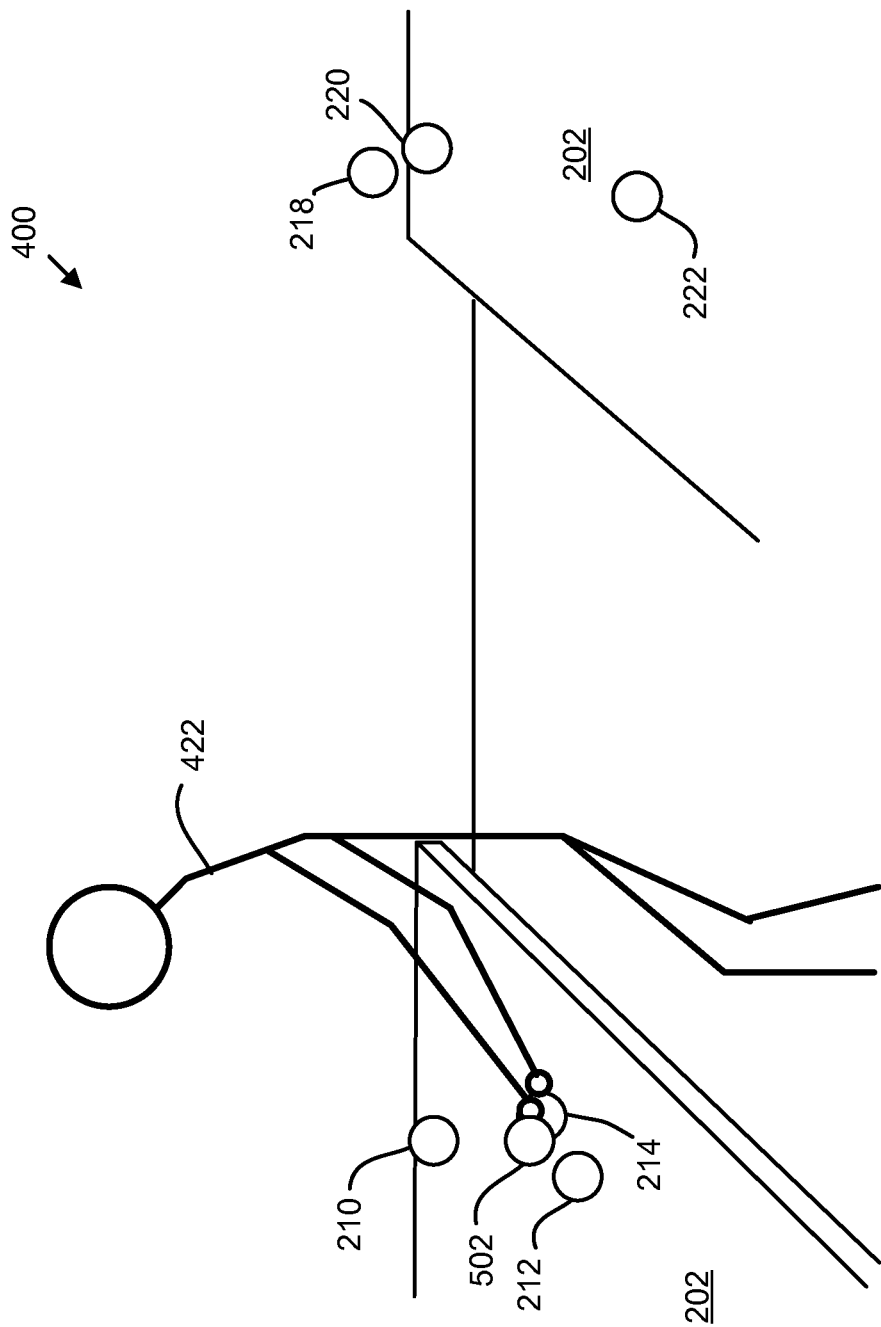
FIG. 6 is an abstracted perspective view of the individual and work area of FIG. 5, according to one embodiment.

FIG. 6 illustrates an abstracted view of the work area 400 of FIG. 5. An abstracted view of the individual 422, counter surfaces 202, cutting board 212, knife 502, carrot 214, cut of meat 210, plates 222, mixing spoon 218, and mixing bowl 220 is depicted. The abstracted view may depict the type of information determined by a tracking component 302. For example, many details may be ignored by the tracking component 302. For example, each object may be treated uniquely and the location of each object may be tracked over time. Likewise, the exact appearance may not be of importance although the location of the hands, head, and other portions of the body are tracked to provide body position information.

According to one embodiment, the tracking component 302 may predict a position of a first portion of the individual based on a position of a second portion of an individual. For example, depending on the position of the individual, a hand may be out of view of a three-dimensional tracking system 104 while a shoulder or elbow may be within view. In one embodiment, the tracking component 302 predicts the location of the hand based on the position of the shoulder or elbow. Similarly, the tracking component 302 may predict a position of a first portion of the individual's body based on movement of the first portion or movement of a different portion of the body. In one embodiment, the tracking component 302 predicts a body position of the individual based on an anatomical model. Using the anatomical model, the tracking component 302 may be able to fill in unknown information based on assumptions from the anatomical model.

In one embodiment, predicting a body position may allow the tracking component 302 to determine a location of an appendage of the individual, even if the appendage is in a blind spot of the three-dimensional tracking system 104. According to one embodiment, one or more mirrors, or an additional three-dimensional tracking system 104 within the work area, may be used to decrease blind spots.

Figure 7:
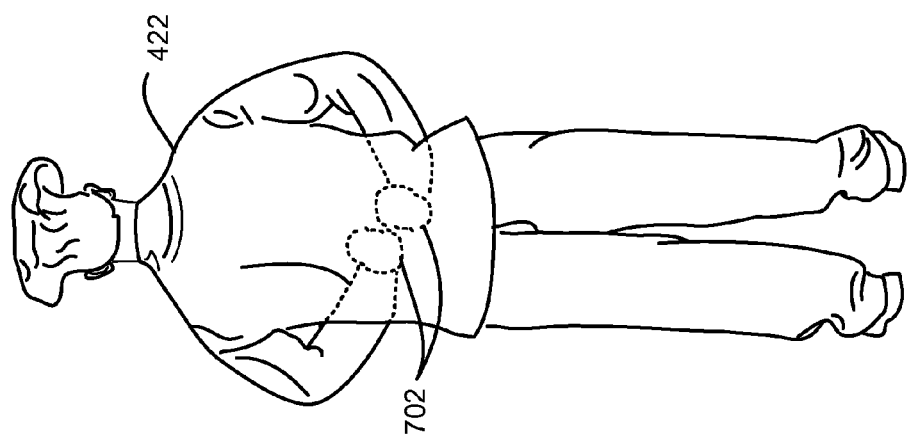
FIG. 7 is a rear perspective view of an individual facing away from a three-dimensional tracking system, according to one embodiment.

FIG. 7 illustrates an example rear view of an individual who is facing away from a three-dimensional tracking system 104. The individual's hands 702 are out of sight and are depicted with dotted lines. According to one embodiment, because the individual's hands 702 are out of sight, or within a blind spot, of a three-dimensional tracking system 104, the three-dimensional tracking system 104 may not be able to determine a location of the hands 702 based on imaging or projection techniques.

However, an anatomical model may be used by the three-dimensional tracking system 104 or tracking component 302 to predict a location of the hands 702 based on a position of the other parts of the individual 422. For example, an anatomical model may include an estimate for the length of the individual's forearms. More specifically, if the three-dimensional tracking system 104 is able to locate an elbow and the angle formed by the angle, the locations of the hands may be predicted based on the predicted distance between the elbow and the hand. Thus, even though the hands are out of sight, the three-dimensional tracking system 104 may be able to continue to track the location of the individual's hands 702 and/or a body position of the individual.

In one embodiment, the tracking component 302 tracks two or more individuals within the work area. Tracking more than one individual may allow the activity monitoring component 102 to identify problems that are based on the actions of more than one individual.

In one embodiment, in addition to using a three-dimensional tracking system 104 to track the individual and objects, the tracking component 302 uses an identification tag sensor to detect an identification tag and track a location. In one embodiment, the tracking component 302 may track the location of an individual or object based on detection of an identification tag. For example, one or more identification tag sensors distributed throughout a work area may be used to determine an approximate location of an identification tag and thereby track a location of a corresponding individual or object. The identification tag sensor may detect a variety of types of identification tags such as a radio frequency identification (RFID) tag, a barcode, and/or a quick response (QR) code.

The tracking component 302 may, in some embodiments, track a location of an individual or object based on output from other sensors. For example, output from sensors, such as pressure sensors, proximity sensors, or other sensors, may indicate a location of an individual or object and may be used by the tracking component 302 to track a location of an individual or an object.

Returning to FIG. 3, the activity identification component 304 identifies an activity of the individual and any objects that are affected by the activity. The activity identification component 304 identifies an activity based on information received from one or more of the other components 302, 306-328 and/or from the three-dimensional tracking system 104. For example, the activity identification component 304 may identify an activity based on a location or a movement detected by the tracking component 302 and/or the three-dimensional tracking system 104.

The activity identification component 304 may identify the activity of an individual based on a location of the individual. For example, if an individual is located in a cooking area, the activity identification component 304 may determine that the individual is cooking. Similarly, if an individual is located in a hand washing area, the activity identification component 304 may determine that the individual is washing his or her hands.

The activity identification component 304 may identify the activity of an individual based on a proximity of the individual to an object. For example, if a user is proximal to a counter surface, a knife, and a vegetable, the activity identification component 304 may identify the activity as cutting the vegetable. Similarly, other activities may be identified based on proximity to other objects.

The activity identification component 304 may identify the activity of an individual based on a body position of the individual. In one embodiment, the activity identification component 304 may receive body position information from the tracking component 302 and identify the activity based on the body position. The body position information may include information regarding locations of the appendages of the individual's body, angles of joints, and other information about the body position. In one embodiment, the activity identification component 304 may match a body position of an individual to a body position corresponding to an anatomical model of an individual involved in a specific activity. The activity identification component 304 may determine that the individual is involved in the matching activity.

The activity identification component 304 may identify an activity based on a gesture or movement made by the individual. As used herein, the term "gesture" is given to mean movements or sequential positions of an individual's body performed while engaged in an activity. For example, a user may perform a chopping gesture while cutting food that includes an up and down motion of a hand. A chopping gesture may also include a stationary supporting hand for holding an object that is being chopped. Thus, in one embodiment, the activity identification component 304 identifies a gesture that involves a stationary hand and an up and down movement with another hand as chopping. Other example gestures may include circular motions performed when mixing ingredients, rubbing two hands together while washing hands, or the like.

The activity identification component 304 may identify activities based on one or more sensors in addition to, or alternatively to, using output from a three-dimensional tracking system. Sensors may be located on or in one or more of an individual, a work area object, a food item, or other object. The activity identification component 304 may identify an activity based on output from a flow sensor. For example, the activity identification component 304 may identify an activity as hand washing, washing an object, or other washing activity in response to the flow sensor sensing the flow of water from a faucet. As another example, the activity identification component 304 may identify an activity as hand washing, or washing an object in response to detecting a flow of sanitizer from a dispenser.

The activity identification component 304 may identify an activity based on output from a temperature sensor. In one embodiment, the temperature sensor may be a sensor on an object whose temperature is to be sensed. In another embodiment, the temperature sensor may be a remote temperature sensor to detect a temperature of an object or surface that is not contacting the remote temperature sensor. For example, the activity identification component 304 may identify the activity as a cooking activity in response to detecting a high temperature.

The activity identification component 304 may identify an activity based on output from a proximity sensor. For example, the activity identification component 304 may identify an activity as using a work area object based on the proximity sensor indicating that the individual is near the work area object. The activity identification component 304 may identify an activity based on output from a pressure sensor. For example, the activity identification component 304 may identify that an activity involves use of an object in response to the output from the pressure sensor indicating that the user is manipulating the object. Additionally, the pressure signature output by the pressure sensor may be used by the activity identification component 304 to identify the activity.

In one embodiment, the activity identification component 304 may identify an object involved in an activity based on an identification tag sensor detecting an identification tag on the object. For example, the identification tag sensor may detect an RFID, barcode, or quick response code on a tag of an object and identify the object based on the detected tag. The activity identification component 304 may then identify the activity based on the identified object. For example, if the identification tag sensor detects a tag corresponding to a knife as affected by an activity, the activity identification component 304 may identify the activity as cutting using the knife, washing of the knife, or the like.

The activity identification component 304 may be configured to identify a wide variety of activities. Different embodiments may be configured to identify an activity depending on a specific environment, such as food preparation, manufacturing, or healthcare. For example, some activities may not occur or may not be of interest in some work areas. Some example activities that can be identified by the activity identification component 304 are discussed below.

Returning to FIG. 5, one embodiment of a chopping activity is illustrated. In one embodiment, the activity identification component 304 identifies the individual 422 as performing a chopping activity based on the individual's location near counter surface 202, vegetable 214, and cutting board, as well as based on movement of the knife 502 and the individual's hand in an up and down motion (not shown).

Figure 8:
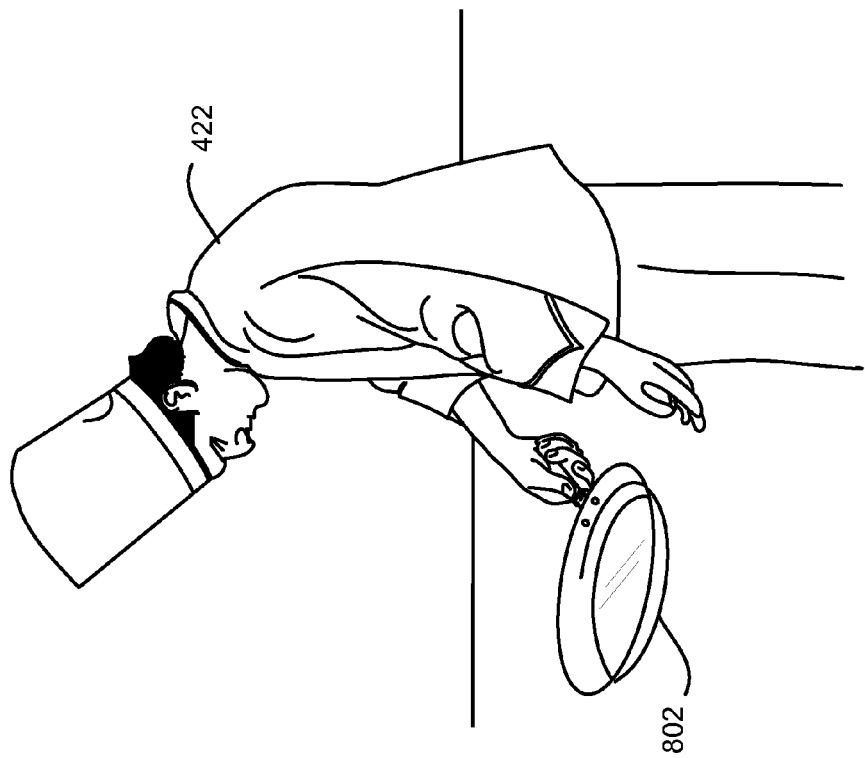
FIG. 8 is a perspective view illustrating an individual performing a cooking activity, according to one embodiment.

FIG. 8 is a perspective view of an individual 422 involved in a cooking activity. The individual 422 is shown holding a frying pan 802. In one embodiment, the activity identification component 304 identifies the individual 422 as involved in a cooking activity based on the individual 422 holding the frying pan, the location of the individual 422 near a stove, and/or output from a remote temperature sensor indicating that the frying pan 802 is at a cooking temperature.

Figure 9:
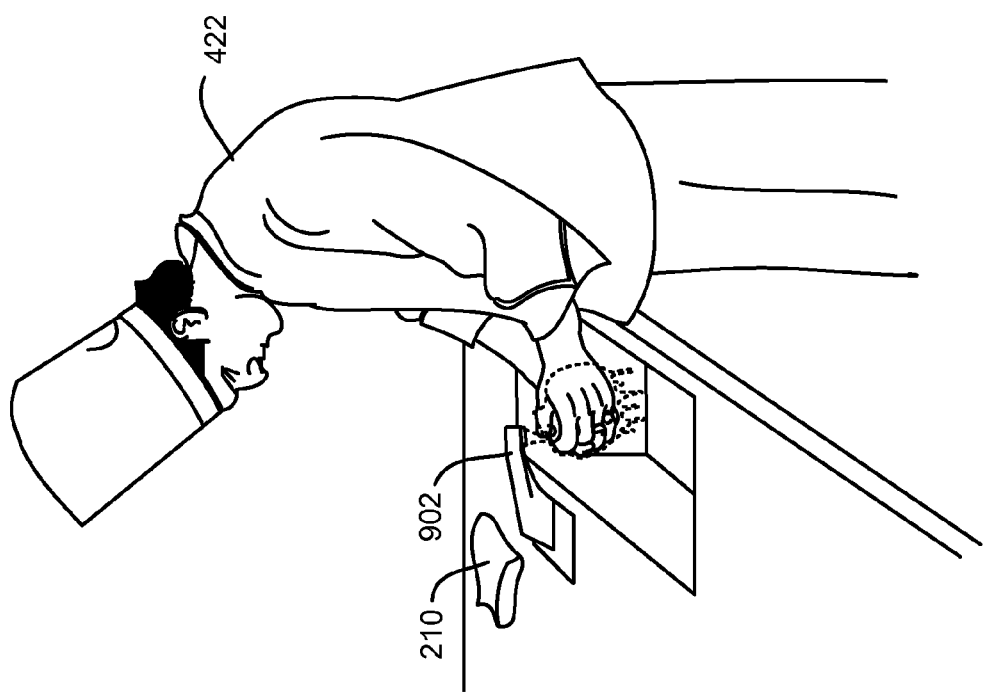
FIG. 9 is a perspective view illustrating an individual performing a hand washing activity, according to one embodiment.

FIG. 9 is a perspective view of an individual 422 involved in a hand washing activity. In one embodiment, the activity identification component 304 identifies the individual 422 as involved in a hand washing activity based on the individual's proximity to a sink, a flow sensor output indicating that water is flowing from the faucet 902, and a gesture of the individual 422 that includes rubbing the hands together. The activity identification component 304 identifying an activity as hand washing may also include determining that the individual has used soap and rubbed the hands together vigorously for a sufficient time period.

The activity identification component 304 may identify other types of washing activities. For example, the activity identification component 304 may determine that an individual is washing an object based on the user rubbing the object and/or applying a cleaning implement or cleaning solution to the object. Similarly, the activity identification component 304 may identify a user's activity as washing a food item. For example, the activity identification component 304 may determine that the user is washing the food item based on the user holding the food item under a running faucet.

The activity identification component 304 may identify a carrying activity. For example, the activity identification component 304 may identify a carrying activity based on movement of an object with an individual from one location to another. In one embodiment, the activity identification component 304 may also determine that the individual is in contact or in sufficient proximity to contact the object.

The activity identification component 304 may identify a mixing activity. For example, the activity identification component 304 may identify a mixing activity based on the individual holding a spoon or other mixing implement and moving the spoon in circular motions within a bowl or other container.

The activity identification component 304 may identify an activity that includes contact between objects. According to one embodiment, the activity identification component 304 identifies an activity that includes contact between individuals, objects, and/or work area surfaces. The activity identification component 304 may identify contact between the individual and an object of the one or more objects. The activity identification component 304 may identify contact between the individual and a surface of the work area, such as a counter surface. The activity identification component 304 may identify contact between the individual and a floor, such as the hand of the individual and the floor. The activity identification component 304 may identify contact between the individual and a sink. The activity identification component 304 may identify contact between the individual and a waste product. The activity identification component 304 may identify contact between an object and another object. The activity identification component 304 may identify contact between an object and a surface of the work area.

In one embodiment, the activity identification component 304 may determine that an object has contacted another object based on the objects being within a threshold proximity. In one embodiment, the activity identification component 304 may determine that an object has contacted another object based on the two objects having corresponding movements. For example, if an object is determined to be close to a hand of an individual and the object substantially follows the movements of the hand, then the activity identification component 304 may determine that the object is in contact with the individual. Additionally, if an object accelerates or changes direction when it comes into proximity with another object, the activity identification component 304 may determine that the two objects have contacted each other.

In one embodiment, the activity identification component 304 may identify a user's activity as using a tool. For example, the activity identification component 304 may determine that the user is using the tool based on the user contacting the tool. The activity identification component 304 may also determine that the tool is being used on a specific object based on the user manipulating the tool to contact the object. The activity identification component 304 may identify a user's activity as assembling of parts. For example, the activity identification component 304 may determine that the user is assembling parts based on the user holding the parts and causing them to contact each other.

According to one embodiment, the activity identification component 304 may identify an activity as having a risk of contamination. For example, the activity identification component 304 may determine that an activity has a risk of contaminating an individual, an object, or a portion of the work area. In one embodiment, the activity identification component 304 may determine that anything that comes into contact with raw meat or a raw animal product is contaminated. In another embodiment, the activity identification component 304 may determine that anything that comes into contact with unwashed hands is contaminated.

In one embodiment, the activity identification component 304 may identify an activity based on a previous or subsequent action. For example, the activity identification component 304 may identify an activity differently based on an action or activity immediately preceding or immediately following the activity. Similarly, the activity identification component 304 may identify the activity based on a sequence of interactions between the individual and the one or more objects. For example, if a user grabs a knife, positions a cutting board, and places a material on the cutting board, the subsequent hand motion of the individual may be determined to be cutting the material, whereas similar detection motion of the individual holding a knife following different actions may be determined to be washing the knife.

The material identification component 306 identifies a material within the work area. The material identification component 306 identifies the material based on information obtained or determined by the three-dimensional tracking system 104, tracking component 302, or other component.

In one embodiment, the material identification component 306 identifies a material of an object or other material within the work area based on a captured image. For example, an image captured by a camera of the three-dimensional tracking system 104 may be provided to the material identification component 306 for processing and identification of materials. In one embodiment, a high-resolution camera may be used to capture images of specific objects or materials to provide greater detail in allowing the material identification component 306 to identify a material. For example, a high-resolution or zooming still camera may be used to obtain highly detailed pictures of objects or materials. Similarly, ranging information from a ranging system or information from a sensor 106 may also be used by the material identification component 302 to identify a material.

The material identification component 306 may identify the material based on a variety of detected attributes of an object. Some example attributes that the material identification component 306 may use to identify the material include attributes such as a color of the material, a pattern of the material, a shape of the material, a texture of the material, a size of the material or corresponding object, and the like. The material identification component 306 may identify the material based on a color of the material. For example, the material identification component 306 may detect a color of a material in a captured image and compare the color with a database to determine what types of materials have a similar color. The material identification component 306 may identify the material based on a pattern of the material. For example, the material identification component 306 may detect a pattern in an image or in three-dimensional data provided by the three-dimensional tracking system 104 and identify the material based on materials that may have the same or similar patterns.

The material identification component 306 may identify the material based on a texture of the individual. The texture of the material may be determined based on an image and/or three-dimensional data obtained by the three-dimensional tracking system 104. The material identification component 306 may then identify the material based on the texture matching or being similar to a specific type of material. The material identification component 306 may identify the material based on a shape of the material or object. For example, the shape of the material in the captured image or as determined by three-dimensional data from the three-dimensional tracking system 104 may be used to match the material or object with a material or object having a similar shape. In one embodiment, the material identification component 306 may use one or more of color, pattern, texture, shape, size, or the like to identify the material.

Example materials that the material identification component 306 may identify include raw meat, cooked meat, animal products, baked goods, fruits, vegetables, or other food material or ingredients. In some embodiments, the material identification component 306 may also identify bodily fluids, chemicals, plants, allergens, metals, wood, or other materials. For example, in a health care environment it may be useful to identify blood or other bodily fluids or products to determine sanitary states of contacted surfaces.

Figure 10:
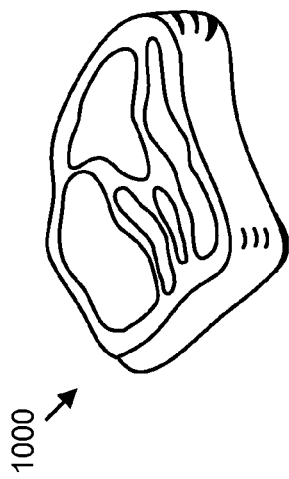
FIG. 10 is a perspective view of a cut of meat, according to one embodiment.
Figure 11:
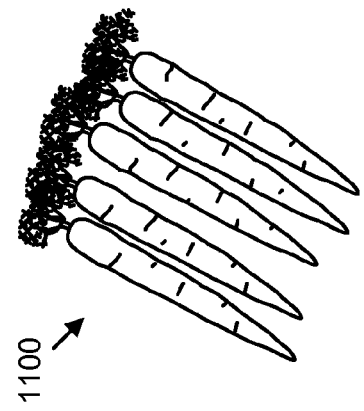
FIG. 11 is a perspective view of a group of carrots, according to one embodiment.

FIGS. 10 and 11 illustrate example materials which may be identified by the material identification component 306. FIG. 10 is a perspective view of a cut of meat 1000. The cut of meat 1000 is shown with a marbled pattern. In one embodiment, the cut of meat 1000 includes various colors of reds and whites. According to one embodiment, the material identification component 306 receives an image of the cut of meat 1000 as it sits within a work area. The material identification component 306 may then perform an image analysis of the cut of meat 1000 to determine that it comprises raw meat, based on the color, pattern, and/or shape of the cut of meat. In one embodiment, three-dimensional data from the three-dimensional tracking system 104 that indicates a three-dimensional shape or texture of the cut of meat 1000 may also be used.

FIG. 11 is a perspective view of some carrots 1100. The carrots 1100 have a bright orange color and an oblong shape. The carrots also have a surface pattern of ridges and bumps as well as greens at an end. According to one embodiment, the material identification component 306 receives an image of the carrots 1100. The material identification component 306 identifies the carrots 1100 as carrots based on their color, shape, and texture.

According to one embodiment, the material identification component 306 may identify a material as sanitary, unsanitary, or the like. For example, the material identification component 306 may identify material as unsanitary if it has a high risk of contaminating another surface through proximity or contact. In one embodiment, the material identification component 306 identifies raw meat as unsanitary due to a risk of transferring harmful bacteria to another surface through contact. Similarly, other raw animal products, bodily fluids, or other materials may also be identified as unsanitary.

The material identification component 306 may identify material as having a low risk of contaminating through proximity with an object of the one or more objects and the individual. For example, many fruits and vegetables have very low risks of harboring harmful bacteria, and thus may be identified by the material identification component 306 as sanitary. Similarly, baked goods, many plant products, or other materials may be identified by the material identification component 306 as sanitary.

According to another embodiment, the material identification component 306 may identify a material as an allergen or including an allergen. For example, the material identification component 306 may identify some nuts, flowers, leaves, or other materials as a specific type of allergen. In one embodiment, specific allergens may be prohibited in a work area and the material identification component 306 may be configured to identify those allergens. For example, peanuts may be prohibited in a work area that is manufacturing peanut free foods.

The procedural component 308 determines whether a contamination or violation of a procedural rule has occurred within a work area. For example, the procedural component 308 may identify errors such as handling raw meat and then handling plates, putting raw meat on wrong counters, or the like. In one embodiment, the procedural component 308 determines whether an activity detected by the activity identification component 306 violates one or more procedural rules pertaining to one or more of the individual, the work area, and the one or more objects. In another embodiment, the procedural component 308 determines that an object of the one or more objects is contaminated based on tracked locations of the one or more objects and the individual.

In the case of determining whether an activity violates a procedural rule, the procedural component 308 compares the activity and/or circumstances within a work area to a procedural rule. The procedural rule may include one or more requirements in order to violate the procedural rule. For example, a proximity requirement of a procedural rule may require that objects and/or an individual are within a certain proximity from each other. The proximity requirement may be based on the locations of objects, individuals, and/or logical areas within the work area as tracked by the tracking component 302. Other requirements may include sanitary requirements, location requirements, movement requirements, body position requirements, or the like. One or more procedural rules may be stored by the procedural component 308. A variety of example procedural rules are discussed below.

A procedural rule may define a violation of a food handling procedure, a sanitary rule, or a contamination rule. For example, a contamination rule may define work area situations or activities with potential to contaminate a food item. Similarly, a procedural rule may define potential contamination of a lab sample. The procedural component may compare a work area activity, or circumstances within a work area, to the procedural rule and determine whether a violation of a food handling procedure, a sanitary rule, and/or a contamination rule has occurred. In one embodiment, a procedural rule may define proper kitchen conditions. For example, the procedural rule may include requirements for a maximum number of individuals, a temperature range, and/or locations for certain types of items within the kitchen work area.

A procedural rule may define a violation of proper tool usage, an assembly procedure, or the like. For example, a procedural rule for a manufacturing work area may include requirements that a specific tool is not to be used during one or more assembly steps. For example, the tool may provide excessive torque for the tightening of a certain type of fastener. The procedural component 308 may determine whether the tool is being used and whether the fastener on which it is being used is of a certain type. If the conditions meet the requirements of the procedural rule, the procedural component 308 may determine that a violation has occurred.

A procedural rule may define violation of a rule against the presence of unauthorized individuals in a work area. The procedural rule may define the presence of an unauthorized individual based on a determination that the individual is not wearing a badge. For example, the tracking component 302 may track an individual within the work area and an identification tag sensor may determine that the individual is not wearing a badge that includes an identification tag. Alternatively or additionally, the procedural rule may define the presence of an unauthorized individual based on a determination that an individual's face does not match a facial recognition map of any authorized individuals. For example, the tracking component 302 may obtain a facial recognition map of an individual and the procedural component 308 may compare the facial recognition map to recognition maps of authorized individuals stored within a storage device. If the facial recognition map does not have a match, the procedural component 308 determines that the individual is not authorized. Similarly, a procedural rule may define unauthorized performance of an activity. For example, only certain individuals may be allowed to operate certain machinery or perform certain activities with a work area.

A procedural rule may define a violation of a rule against theft. The rule against theft may define theft by an employee and/or theft by a customer. For example, theft by an employee may be defined differently than theft by a customer because employees may be authorized to do more with store merchandise without payment than a customer. For example, a bartender within a bar is authorized to obtain beverages from behind a counter and pour drinks for customers while a customer is not authorized to do so. However, a bartender may not be allowed to take payments from customers and keep them as a tip. In one embodiment, the procedural rule may define a violation of a rule against theft as a customer accepting cash from a customer and failing to place it within a cash register within a defined time period.

A procedural rule may define violation of a law. Examples of laws which may be violated include food handling regulations, criminal laws, packaging regulations, manufacturing regulations, or the like. In one embodiment, the procedural rule may define requirements that constitute a violation of a law, and the procedural component 308 may compare activities and/or circumstances within a work area to the defined requirements.

A procedural rule may define a productivity rule. In one embodiment, a productivity rule may include rules regarding late arrival, early departure, activity in the work area, or the like. For example, the procedural rule may include requirements that an individual be present within the work area within a defined time period of the beginning of the individual's shift. The procedural component 308 may determine whether the individual is present at the proper time, leaves early, or has not physically moved enough for a certain time.

A procedural rule may define use of a forbidden substance. Example rules against forbidden substances may include requirements indicating whether a substance is present in the work area or how a specific drug is used. For example, the material identification component 306 may identify a forbidden substance, and the procedural component may compare the presence of the substance to a procedural rule to determine that the substance is forbidden. In one embodiment, labels on packaging may be used to identify a forbidden substance. As another example, a procedural rule may define smoking, drinking alcohol, or using another drug, and the procedural component 308 may detect whether an action that corresponds to the definition has occurred in the work area. For example, a procedural rule may define smoking as holding an elongated and/or cylindrical object up to an individual's mouth.

In one embodiment, a procedural rule defines a combination of one or more work area conditions that comprise a violation. The procedural component 308 may compare current conditions within a work area to the procedural rule to determine whether the defined combination of work area conditions is present. The work area conditions may include a variety of conditions as determined by the procedural component 308, or any of the other components 302-306 and 310-328 of the activity monitoring component 102.

Examples of work area conditions which may be detected and compared to a procedural rule include a sanitary state of an object, a sanitary state of an individual, a sanitary state of a work area object or work area surface, a sterile state of a work area object or surface, a proximity between objects, a location of an object in the work area, a current activity, a previous activity, conditions indicated by output from a remote temperature sensor, conditions indicated by output from a proximity sensor, conditions indicated by output from a pressure sensor, conditions indicated by output from an identification tag sensor, conditions indicated by output from a flow sensor, and the like.

In the case of determining whether an object is contaminated, the procedural component 308 may analyze tracked locations of the object, as well as tracked locations of other objects and/or an individual, to determine whether the object has been contaminated. In one embodiment, the procedural component 308 determines whether an object is contaminated based on the material of the object. For example, a vegetable may be contaminated by coming in close proximity to raw meat, while a cut of raw meat may not necessarily be contaminated because it is close to some other raw meat.

In one embodiment, the procedural component 308 determines that an object is contaminated based on contact with a contamination source. The contamination source includes, or has a high risk of including, a material that does not belong with the object. For example, a contamination source may have a high risk of having high bacteria levels and high bacteria levels may not belong on food material that will be consumed without cooking. The contamination source may include another object, an individual, a work area object, or the like. For example, work area objects may include a counter surface, floor, sink, or other work area surface or object.

In one embodiment, the procedural component 308 will determine that an object is contaminated based on the location of the object within a logical area of the work area. For example, the procedural component 308 may determine that a counter surface in the logical area has a high risk of harboring high bacteria levels and that the object has contacted the counter surface. The procedural component 308 may determine that an object is contaminated based on the object's location within a meat handling area, a hand washing area, an allergen area, a non-sterile area, or the like.

Some examples of contact with an object that the procedural component 308 may determine to be contaminating are provided below. The procedural component 308 may determine that the object should be sterile but contacted a non-sterile object. The procedural component 308 may determine that the object should be sanitary but contacted unwashed hands. The procedural component 308 may determine that the object should be sanitary but has contacted raw meat. The procedural component 308 may determine that the object should be sanitary but has contacted raw animal products. The procedural component 308 may determine that the object should be allergen free but contacted an allergen. The object may be a lab sample and the procedural component 308 may determine that the lab sample has contacted an object that has contacted another lab sample. The procedural component 308 may determine that the object should be sterile but has contacted a material comprising bodily fluids.

According to one embodiment, the procedural component 308 determines that the object is contaminated based on determining that there is high risk that the object has material that does not belong with the object. In one embodiment, the procedural component 308 determines that there is a high risk based on the location of the object in a logical area of the work area. For example, if a raw vegetable is carried into the raw meat area 410 of FIG. 4, the procedural component 308 may determine that the raw vegetable is contaminated.

In one embodiment, the procedural component 308 determines that there is a high risk based on a proximity to a contamination source. For example, the object may be a plant product and the procedural component 308 may determine that there is a high risk of contamination because the plant product is proximal to a raw animal product. Turning to FIG. 5, a vegetable 214 is being chopped by the individual 422 with a raw cut of meat 210 resting nearby. The procedural component 308 may determine that the vegetable 214 and the cut of meat 210 are too close and may determine that there is a high risk of contamination of the vegetable. Similarly, the procedural component 308 may determine that the knife 502, cutting board, and counter surface 202 all have a high risk of contamination.

The procedural component 308 may determine that an object has a high risk of contamination because it is proximal to a hand washing area. In FIG. 9, a cut of meat 210 is shown resting on a counter near a hand washing sink. In one embodiment, the procedural component 308 may determine that the cut of meat 210 is contaminated, or has a high risk of being contaminated, based on its proximity to the hand washing sink. Similarly, the procedural component 308 may determine that the cut of meat 210 is contaminated, or has a high risk of being contaminated, based on its proximity to the hand washing activity of the individual 422.

The procedural component 308 may determine that an object that includes a lab sample has a high risk of contamination based on its proximity to another lab sample. For example, lab samples used for research in a laboratory may be kept separate so that independent tests may be performed. The procedural component 308 may determine that the lab samples are too close and may determine that one or both are contaminated.

In one embodiment, the procedural component 308 determines that the object is contaminated based on sequential contact between the object, one or more intermediate objects, and a contamination source. For example, even if a vegetable is not contacted or brought within proximity of raw meat, the procedural component 308 may determine that the vegetable is contaminated based on contact with an object, hand, or surface that has contacted the raw meat prior to contacting the vegetable.

One or more procedural rules may define scenarios where in increased risk of a violation or contamination is present, even if the violation or contamination has not yet occurred. For example, a procedural rule may define when current activities present an increased probability of a problem or violation. Thus, a recommendation or warning may be provided even before a negative event occurs. For example, the procedural component 308 may detect the increased probability and cause a notification component 310 to provide a warning indicating of proximity between a contamination source and a sterile surface. The procedural rules may define other types of hazards such as liquid splashing. A voice notification may state that "you are washing X in this sink while Y is within 2 feet; be careful of splashing." Similarly, the warning may include a voice warning that states "you are carrying meat into the vegetable preparation area; bad idea!" The corresponding individual may then be able to stop and prevent a violation that might otherwise have occurred.

The notification component 310 provides notification that indicates one or more of a contamination, an occurrence of a violation, a status of an object or individual, or the like. The notification component 310 may receive information regarding a contamination, violation, or status as determined by the procedural component 308 or other component and may provide a notification regarding the occurrence. The notification component 310 may provide notifications of contamination, violation, or status component in real-time.

According to one embodiment, the notification component 310 provides a notification by providing a data file that includes information regarding a violation, contamination, status, or the like. In one embodiment, the data file may be stored within memory. For example, the file may include a time, individual involved, objects involved, type of violation, or other information, as determined by one or more of the components 302-324 of the activity monitoring component 102. In one embodiment, the file may be stored for later access by an employer, government, or other monitoring entity.

In one embodiment, a notification is provided to a remote location, such as the remote computing system 110. For example, a remote computing system 110 may be used by an employer, government, or other organization to determine whether a contamination or violation has occurred. A data file may be provided to the remote location that provides information about the violation or contamination.

In one embodiment, the notification component 310 provides notification within the work area. For example, the notification component 310 provides a notification within the work area such that an individual 422 working with the work area may be able to observe the notification and know that the violation or contamination has occurred. The notification component 310 provides the notification in response to the procedural component 308 determining that a violation or contamination has occurred.

According to one embodiment, the notification component 310 may provide a visible notification within the work area. In one embodiment, the notification component 310 may cause a spotlight, laser pointer, indicator light, display, or other output device to provide a visible output. In one embodiment, the notification component 310 may spotlight an object, individual, or surface that has been contaminated, as determined by the procedural component 308. For example, a spotlight, laser pointer, or the like may be used to point to an object that has been contaminated. An individual may be able to discard, wash, or otherwise remedy the situation of the contaminated object. In one embodiment, the notification component 310 may spotlight an object, individual, or surface that has been affected by a violating activity as determined by the procedural component 308.

In one embodiment, the notification component 310 may change a status of an indicator light on an object to indicate the status of the object. For example, an object that may be used as a tool, cooking implement, cleaning implement, or the like may include an indicator light. An indicator light may also be included in a badge, work area object, or at another location to indicate a status of an individual, counter surface, or the like. The indicator light includes a small light emitting diode (LED) or other lamp. Circuitry embedded in the object may allow the notification component 310 to wirelessly control the state of the indicator light. For example, the notification component 310 may provide a wireless signal to the object to cause the state of the light to change to indicate a contaminated status when the procedural component 308 determines that the object is contaminated. In one embodiment, different colors may be used to indicate whether the object needs to be cleaned, discarded, or the like. Similarly, a state of the lamp, such as on, off, or blinking, may indicate the status. As an example, the cutting board 212 of FIG. 5 may include an indicator light whose state may be changed to a flashing red color to indicate that there has been meat on the cutting board or a plurality of other states.

In one embodiment, a display, such as the display 228 of FIG. 2, may be used to provide a visible notification of a contamination, violation, or other occurrence or status. For example, the notification component 310 may display a diagram of the work area on the display 228. Locations of objects, individuals, work area objects, and/or logical areas may be indicated on the diagram. The notification component 310 may change a color or other display attribute of an object, individual, or work area object to indicate contamination, a violating event, or other status. For example, if an individual performs an activity that results in the contamination of a food item, the diagram may be updated to display the individual and food item with a red color.

Using the spotlights, laser pointers, indicator lights, or diagrams, the notification component 310 may be able to indicate safe, unsafe, or unknown spots on surfaces. Individuals within the work area may then be able to take actions with regard to different sources to reduce chances of violations or contaminations.

According to one embodiment, the notification component 310 may provide an audio notification within the work area. For example, the notification component 310 may output an audio notification on the speakers 232 of FIG. 2. In one embodiment, the notification component 310 outputs a voice notification that indicates information regarding a contamination, violation, or status. For example, the voice notification may state a name of an individual, identify an object type and location, and state a procedural rule that has been violated. Similarly, the voice may state a location in the work area, material, type, status, or other information to provide a notification of the violation, contamination, or status. The voice notification may also state a rule or proper procedure to be followed in the future. An individual may be able to respond or learn from the event and remedy the current situation. For example, FIG. 9 illustrates a individual 422 washing hands near a cut of meat 210. The notification component 310 may provide a voice notification stating that the cut of meat 210 is too close to the hand washing location and is in danger of being contaminated.

According to one embodiment, the notification component 310 automatically issues a citation in response to the procedural component determining that there was a procedural violation or contamination. For example, the citation may indicate the violation of a health regulation, manufacturing regulation, contamination of a lab sample, violation of a training rule, or other error within the work area. The citation may include information regarding a specific procedural rule, evidence of the violation as gathered by the activity monitoring system 100, and/or a fine to be paid by an individual or establishment. In one embodiment, the citation may be issued by a governing authority such as a government. According to one embodiment, the notification component 310 and other components may work together to automatically detect, document, and issue citations for health violations or other violations.

In another embodiment, the notification component 310 provides a notification by issuing a report. The report may include a number of violations at an establishment within a time period. The report may include a list of violations with descriptions and/or severity for each violation. In one embodiment, the report may include the number of violations of an individual within a time period. For example, an individual may be identified as a "bad actor" or the cause of a disproportionate share of problems in the work area. A report may also include statistical information on compliance or noncompliance with specific procedures or problems associated with particular individuals or particular activities (e.g., one individual may have a tendency to performing hand washing in food sinks)

The status component 312 maintains a status of an object, a portion of a work area, an individual, or the like. The status maintained by the status component 312 may include a current status based on determinations made by the tracking component 302, the activity identification component 304, the material identification component 306, the procedural component 308, or another component. For example, the status component 312 may update a status for an object in response to the procedural component 308 determining that the object is contaminated. The status maintained by the status component 312 may include information regarding whether an object, individual, or work area surface is contaminated, sterile, allergen free, or the like. Similarly, the status component 312 may update a status for an object in response to the tracking component 302 detecting a movement of the object to a new location within a work area.

In one embodiment, the status component 312 maintains a database with an entry for an object, individual, and/or work area surface tracked by the tracking component 302. For example, an entry for the cut of meat 210, cutting board 212, vegetable 214, and other objects may be included within a database. The status component 312 may update a status entry when a corresponding activity, movement, or other event occurs within the work area.

A status for an object, individual, or work area surface maintained by a status component 312 may include a safe, unsafe, or unknown status. For example, the status component 312 may maintain a status that indicates the safety for consumption or contact with something that will be consumed by a human. The safe status may indicate that there is little risk of danger from eating or handling food using an object. The unsafe status may indicate that there is a known high danger for eating an object or for eating off of an object, such as a plate or fork. The unknown status may indicate that not enough information about the object is known. In one embodiment, the activity monitoring component 102 may treat an unknown status similar to an unsafe status. In another embodiment, the status component 312 may maintain a status that includes a contaminated, not contaminated, and unknown status for each tracked object, individual, or the like.

The status component 312 may update a status based on an activity identified by the activity identification component 304. The activity identification component 304 may identify an activity that comprises cleaning an object, surface, or individual, and the status component 312 may update a corresponding contamination status to indicate that the object, surface, or individual has been cleaned. For example, the status component 312 may update a status to a safe or non-contaminated status in response to the cleaning. The activity identification component 304 may identify an activity that includes interaction between a first object and a second object, and the status component 312 may update a contamination status of the second object based on the contamination status of the first object. Similar status updates may be made with respect to interaction between individuals, objects, and/or portions of a work area. In one embodiment, the status component 312 updates the contamination status of an object, individual, or portion of a work area based on the procedural component 308 determining that an activity violates a procedural rule that defines violation of a contamination rule.

According to one embodiment, the notification component 310 indicates the contamination status of an object, individual, or portion of the work area. For example, the notification component 310 may spotlight any object, individual, or portion of a work area that is contaminated and/or needs to be cleaned. As another example, a diagram on a display may be updated to indicate the status of each tracked object, portion of the work area, and/or individual in the work area.

In one embodiment, a status component 312 maintains a tracking priority for each tracked object, individual, or portion of the work area. For example, some tracked entities within the work area may be of more importance than others. For example, because individuals generally do most of the moving and activities within a work area, they may have a higher tracking priority than a work area surface that does not move. Similarly, objects or individuals that are contaminated or in an unsafe state may need to be tracked more closely to ensure that other objects, or portions of the work area are not contaminated. In one embodiment, a tracking component 302 may receive the tracking priority and may track an individual, object, or portion of the work area with a higher tracking priority more accurately than an object, individual, or portion of the work area that has a lower tracking priority. For example, the tracking component 302 may more frequently check a location of an object with a higher tracking priority.

As another example, the tracking component 302 may more precisely determine a location in space of an object with a higher tracking priority.

In one embodiment, the status component 312 may provide a status of an object, individual, or portion of the work area to the procedural component 308. The procedural component 308 may use the status information to determine whether a contamination or violation has occurred. In one embodiment, the procedural component 308 may include the status component 312.

The individual identification component 314 identifies an individual in the work area. The individual identification component 314 may identify an individual based on physical attributes, facial recognition, or based on an identification tag or badge. For example, the individual identification component 314 may identify an individual based on images captured by a camera, such as a camera of a three-dimensional tracking system 104. The individual identification component 314 may analyze the image to determine one or more facial features and use those facial features to substantially uniquely identify the individual. The individual identification component 314 may also determine one or more other physical characteristics, such as height, proportional body dimensions, or other characteristics to identify an individual. In one embodiment, three-dimensional features obtained by a range finding device or other tracking system may also be used to identify an individual. In another embodiment, an identification tag sensor may be used to detect an identification tag on an individual and thereby identify the individual.

In one embodiment, the individual identification component 314 may identify each individual that enters a work area. For example, when a worker or other individual enters the work area the individual identification component 314 may determine one or more attributes of the individual. The individual identification component 314 may compare the attributes to one or more stored attributes to determine the identity of the individual. If there is a matching individual, the individual identification component 314 determines the identity of the individual to be the same as the matching individual. If there is no matching individual, the individual identification component 314 may create a new entry with the determined attributes.

In another embodiment, the individual identification component 314 may identify an individual once a violation or contamination has occurred. Individuals that cause a problem or error may be identified and identity information may be logged. For example, the individual identification component 314 may determine attributes of an individual, store those attributes, and/or attempt to locate a corresponding entry for that individual in response to determining that a violation or contamination caused by the individual has occurred.

The history component 316 maintains a history of the work area. The history component 316 may maintain a history that includes information regarding past locations, contact between tracked objects or individuals, activities or other information. For example, the history component 316 may store location, status, cleaning, temperature, material type, identification information, or the like for each object, individual, and/or portion of a work area. In one embodiment, a time of a washing or cleaning of an object, individual, or surface may be stored within the history. In one embodiment, the history may include information about contact between objects and/or individuals.

According to one embodiment, the history component 316 maintains a history which allows reconstruction of what has occurred within the work area. In one embodiment, one or more of the other components may be able to access the history for their respective functions. For example, the procedural component may analyze the history to determine whether a violation or contamination has occurred. The status component 312 may determine a status of an object based on tracked locations and the tracked locations of other objects and/or individuals within the work area.

The activity storage component 318 maintains a database of activities of an individual. For example, all past activities identified by the activity identification component 304 may be stored by the activity storage component. Activities of one or more additional individuals may also be maintained within the database. In one embodiment, the procedural component 308 determines whether the activity violates a procedural rule of the one or more procedural rules based on one or more of the activities of a single individual or of multiple individuals as maintained within the database of activities. In one embodiment, the activity storage component 318 stores information indicating the individual who performed an activity. The activity storage component 318 may analyze the database to determine a productivity of a specific individual. For example, the activity storage component 318 may determine whether the individual is performing a sufficient amount of activities within a work shift.

The tracking storage component 320 stores information regarding tracking of the individual and the one or more objects in the work area. For example, the tracking storage component 320 may store information that indicates the location of an object or individual within a work area. The stored tracking information may be used to prove the occurrence of certain events such as contaminations or violations of procedural rules. The tracking storage component 320 may store the tracking information in local storage or may provide the tracking information to a remote location for storage, such as the remote computing system 110 of FIG. 1.

According to one embodiment, the tracking storage component 320 stores video footage of a work area. For example, a video feed obtained by a video camera of a three-dimensional tracking system 104 may be stored by the tracking storage component 320. More than one video feed may be stored, for example, if multiple cameras are used. The video footage may include video footage of an activity of an individual and/or the location of one or more objects in the work area.

In one embodiment, the tracking storage component 320 stores all video feeds in a temporary storage buffer. After a buffer time, the tracking storage component 320 may delete portions of the video older than a buffer time that do not correspond to a violation or contamination. For example, the tracking storage component may delete portions of video footage older than two hours that do not correspond to a violation. Deletion of video footage may be desirable to decrease storage requirements and/or to reduce privacy concerns. The tracking storage component 320 may receive instructions from a procedural component 308 indicating what time periods are relevant to proving the occurrence of a violation. For example, if multiple activities lead up to and contribute towards a violation, the procedural component may provide a begin and end time for which video should be maintained.

In one embodiment, the tracking storage component 320 may transfer video footage corresponding to a violation to long term storage prior to deletion from a buffer. The video footage corresponding to the violation may include video footage of activities illustrating the violation of the one or more procedural rules. For example, the video footage corresponding to the violation comprising video footage immediately preceding the violation and video footage immediately following the violation.

According to one embodiment, the tracking storage component 320 stores tracking information that includes abstracted information regarding one or more of the work area, the activity of the individual, and the one or more objects. The abstracted information may include information that abstractly indicates the location, position, or orientation of the individual or one or more objects. For example, the abstracted information may include position information that may be used to reconstruct body position or location information that may be used to reconstruct object location, but may not be include imagery or be sufficient to reproduce a photo realistic image of the work area. The abstracted information may include information regarding one or more identified activities. The abstracted information may include information regarding a history of contact between the one or more objects, the individual, and portions of the work area. The abstracted information may be maintained within memory for a longer period of time than video because it may be less memory intensive and/or may include data that is less important for privacy reasons.

In one embodiment, the abstracted information may be used to reconstruct the information object location and information, as indicated in FIG. 6. For example, the abstracted information indicating the location of each object, a location of the individual, and a body position of the individual over time may be used to replay events within the work area in an abstracted form. According to one embodiment, the abstracted version of activities and/or locations within the work area may reduce privacy concerns that may arise when video or imagery of individuals is stored and/or displayed at a later date.

The violation storage component 322 maintains a violation database of violating activities and one or more work area conditions associated with each violating activity. The work area conditions may include information regarding output from sensors, a number of people within the work area, a location of the violation within the work area, objects involved in the violation, the time of day, or the like. For example, each time a violating activity is detected, the violation storage component 322 may add an entry indicating occurrence of the violating activity as well as work area conditions associated with the violation. In one embodiment, all available types of data obtained by sensors and other data regarding the work area at or around the time of the violation is saved and associated with the violation.

According to one embodiment, the violation storage component 322 analyzes the violation database to identify trends or correlations that may indicate problems which may be resolved to improve compliance with procedural rules. In one embodiment, the violation storage component 322 analyzes the violation database to identify a combination of the associated workplace conditions having a correlation to a violating activity. For example, the violation storage component 322 may be able to determine that a specific error occurs often around the same time of day and when there are more than a specific number of individuals. Efforts to take a break at that time and/or reduce the number of individuals in the kitchen may help reduce occurrence of violations. In one embodiment, the violation storage component 322 analyzes the violation database to identify a procedure having a high correlation to a violating activity. For example, the violation storage component 322 may identify that individuals often make errors when preparing a specific dish. The procedure in place for the dish can then be reviewed and modified.

In one embodiment, the violation storage component 322 analyzes the violation database to identify a physical layout feature having a high correlation to a violating activity. In one embodiment, the violation storage component 322 analyzes the violation database to identify a location within the work area having a high correlation to a violating activity. For example, the violation storage component 322 may determine that a large number of violations are occurring at a specific location in the work area or near a specific physical layout feature. Identification of such problem areas may allow for a reworking of the work area to be more efficient and/or reduce likelihood of violations. In one embodiment, the violation storage component 322 analyzes the violation database to identify an individual having a high correlation to a violating activity. For example, the violation storage component 322 may identify an individual having a high frequency for using unwashed hands. The violation storage component 322 may also identify procedures that frequently occur and result in violations.

In one embodiment, a violation storage component 322 may identify work area conditions which represent a high risk of violation. The violation storage component 322 may generate a procedural rule that includes requirements that correspond to the work area conditions related to the high risk of violation. The procedural component 308 may detect that the requirements of the procedural rule have been met and the notification component 310 may provide a warning within the work area that there is a high risk that a violation may soon occur. Individuals within the work area may then be able to modify their actions to ensure that a violation does not take place. For example, the violation storage component 322 may determine that when two types of objects come within a specific non-contaminating proximity and when there are more than four individuals in the work area, there is a high risk that a violation will occur. The two types of objects may include a sterile and a non-sterile object. The procedural component 310 may detect these conditions and provide a warning that a violation might occur based on the proximity of the objects and/or any other associated conditions.

The violation storage component 322 may assist in the identification of work area conditions that may cause a violation. Additionally, the violation storage component 322 may be able to recognize warning signs that a violation is about to occur and allow the notification component 310 to provide a warning to prevent occurrence of the violation. Thus, not only can activities or contamination be monitored, but violations and contaminations can actively be prevented by the activity monitoring component 102.

Although the history component 316, activity storage component 318, tracking storage component 320, and violation storage component 322 and their associated databases or data files are described separately, they may also be combined within a single component and/or database. In one embodiment, for example, the history component 316, activity storage component 318, tracking storage component 320, and violation storage component 322 may all be included within the history component 316. Similarly, the history, activity database, tracking storage database, and/or violation database may all be included within one database.

The pest detection component 324 detects a pest within the work area. The pest detection component 324 may use the three-dimensional tracking system 104, sensors 106, cameras, or the like to detect a pest. For example, the pest detection component 324 may identify an object as a pest based on one or more of object recognition in an image, a location within the work area, how an object moves, or the like. For example, some pests tend to stick to corners or other specific locations within a work area. Similarly, pests may have characteristic manners in which they move through a work area. In one embodiment, the pest detection component 324 may identify an object as a pest when it appears to move without being manipulated by an individual. Some examples of pests that may be detected by the pest detection component 324 include rodents, insects, or the like. In one embodiment, the pest detection component 324 may notify the procedural component 308 of the presence of a pest, and the procedural component 308 may determine that a violation has occurred based on the pest detection component detecting the pest.

The tracer detection component 326 detects a tracer material. The three-dimensional tracking system 104 may include the tracer detection component 326. In one embodiment, the tracer material includes a material that transfers to a contacting surface in response to contact with the tracer material. For example, the tracer material may include a dye, powder, or other material that transfers to a new object or surface when contacted. Example tracer materials include a powder dye, a liquid dye, and/or a UV detectable dye.

The tracer trigger component 328 may trigger detectability of the trigger material. For example, the tracer material may be difficult or impossible to detect during normal activity within a work area. This may allow a true test of procedures within a work area because individuals may not be able to tell whether an object or material has a tracer material on it. The tracer trigger component 328 may trigger detectability at a desired time. For example, the tracer trigger component 328 may trigger detectability at the end of a work area training session. In one embodiment, the tracer trigger component 328 may include an ultra-violet (UV) source, and the tracer material may include a UV detectable tracer. For example, the tracer material may be clear or colorless when UV light is not available and may then be visible when a UV light source is directed towards the tracer material.

In one embodiment, the tracer material may be placed on one or more objects to be treated as contamination sources and the tracer detection component 326 may detect where the tracer material is. For example, over the course of meal preparation in a kitchen, the tracking component 302 may track the locations of the tracer material using the tracer detection component 326 and may thereby determine what objects have effectively become contaminated through contact with the contamination source.

In one embodiment, the tracking component 302 determines that direct contact between a first surface and a second surface has occurred based on the tracer detection component detecting the tracer material on both the first surface and the second surface. Similarly, the tracking component 302 may determine that sequential contact between a first surface, a second surface, and one or more intervening surfaces has occurred based on the tracer detection component 326 detecting the tracer material on the first surface and the second surface.

The procedural component 308 may determine whether an activity violates the one or more procedural rules based on the tracer detection component 326 detecting the tracer material on an object of the one or more objects. Similarly, the activity identification component 304 may determine whether the activity violates the one or more procedural rules based on the tracer detection component 326 detecting the tracer material on the individual.

According to one embodiment, the tracer material may not be safe for human consumption and may be used solely for training purposes. For example, new employees of a restaurant may be provided with training in preparing meals within a work area monitored by an activity monitoring system 100 and mistakes or other details can be detected and pointed out. Thus, training can take place without risking contamination of food that will be used by customers.

The embodiments, methods, systems, and functionality described above are discussed largely in relation to activity and/or contamination monitoring in a kitchen work area. However, similar activity or contamination monitoring within other types of work areas are also possible and fall within the scope of the present disclosure.

Additionally, considerable variation is possible even within kitchen work areas. For example, kitchen work areas may include home kitchens, commercial, kitchens, or any other kitchen. The activity monitoring system 100 may be used for contamination monitoring to detect food contamination, training purposes, general employee monitoring, customer monitoring, or the like. In one embodiment, an activity monitoring system 100 may be installed in a work area in response to a legal violation, food poisoning incident, or other problem at a commercial kitchen.

According to one embodiment, kitchens with employees having a medium skill-levels in food preparation and handling may be most desirable for activity monitoring. For example, high skill-level kitchens with extremely skilled or highly paid chefs may be less susceptible to food handling errors and low skill-level kitchens, such as at McDonalds®, often have extremely tightly programmed preparation procedures. Thus, middle skill-level kitchens, such as at Denny's®, where workers are not extremely skilled but also do not have tightly programmed preparations procedures, may be most desirable for monitoring.

FIG. 12 is a schematic flow chart diagram illustrating one embodiment of a method 1200 for activity monitoring. The method 1200 may be performed by a activity monitoring system 100 with any of the variations discussed herein.

The method 1200 begins and a tracking component 302 tracks 1202 an individual and one or more objects in a work area. The tracking component tracks 1202 the location of the individual and objects using a three-dimensional tracking system 104. The position and/or orientation of the individual may also be tracked. In one embodiment, the tracking component 302 tracks 1202 the locations of objects and the individual in relation to each other and/or in relation to work area objects such as counters, sinks, stoves, or the like. Similarly, the tracking component 302 may track 1202 contact between objects, the individual, and/or the work area.

An activity identification component 304 identifies 1204 an activity of the individual. The activity identification component 1204 may identify the activity based on movements, locations, or positions tracked 1202 by the tracking component 302. In one embodiment, the activity identification component 1204 may detect gestures performed by the individual and determine 1204 an activity based on the detected gesture. The activity identification component 1204 may identify the activity based, at least in part, on input from one or more sensors 106.

A procedural component 308 determines 1206 whether an activity violates a procedural rule. The procedural component 308 determines 1206 whether the activity identified 1204 by the activity identification component 1204 violates a procedural rule by comparing the activity and circumstances within the work area to the procedural rule. For example, a procedural rule may define violation of a food handling procedure. The procedural component 308 may compare the activity, objects affected, or other circumstances to the food handling procedure. If the activity matches the defined violation, the procedural component 308 determines 1206 that the procedural rule has been violated.

The notification component 310 provides 1208 a notification of a violation. For example, the notification component 310 may provide 1208 the notification in response to the procedural component 308 determining 1206 that a violation has occurred. The notification component 310 may provide the notification to a remote location, such as a remote computing system 110, and/or may provide a notification within the work area itself. Notifications within the work area may include visible or audio notifications. For example, visible notifications may be provided 1208 using spotlights, laser pointers, display screens, indicator lights mounted on objects, or the like. Audio notifications may be provided via a speaker and/or sound card. In one embodiment, audio and visible notifications can be used in conjunction to increase awareness of errors and/or provide information that teaches a user how to fix a problem and/or avoid violations in the future by following proper procedures.

FIG. 13 is a schematic flow chart diagram illustrating one embodiment of a method 1300 for contamination monitoring. The method 1300 may be performed by an activity monitoring system 100 with any of the variations discussed herein.

The method 1300 begins and a tracking component 302 tracks 1302 an individual and one or more objects in a work area. The tracking component 302 may track 1302 in a manner similar to that discussed above in relation to FIG. 12.

The material identification component 306 identifies 1304 a material in the work area. The material identification component 306 may identify 1304 the material based on a color, pattern, shape, size, or texture of an object or material. In one embodiment, the material identification component 306 receives an image of the material and analyzes the image to identify 1304 the material. The material identification component 306 may receive three-dimensional information for an object or material from a range finding device and determine a shape, size, texture, or the like based on the three-dimensional information. The determined attributes may then be used in identifying 1304 the material.

A procedural component 308 determines 1306 whether an object is contaminated. The procedural component 308 may determine 1306 whether an object is contaminated based on the movement of the object or the movement of another object, an individual or the like within the work area. For example, proximity or contact between the object and other surfaces may be tracked to determine if the object has contacted an unsanitary or contaminated surface. In one embodiment, the procedural component 308 may determine 1306 whether an object is contaminated based on material types of the object or another object. Similarly, the procedural component 308 may determine 1306 whether an object is contaminated based on a sanitary or contamination status of a contacted surface or object.

A notification component 310 provides 1308 a notification of a contamination. The notification component 310 may provide 1308 a notification remotely, in a visible manner, audible manner, or the like. The notification component 310 may provide 1308 a notification in any manner disclosed in relation to providing 1208 a notification as discussed in relation to FIG. 12 or elsewhere within the present disclosure.

This disclosure has been made with reference to various example embodiments including the best mode. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A non-transitory computer-readable storage medium comprising program code for causing one or more processors to perform a method for activity monitoring, the method comprising:

tracking an individual using a three-dimensional tracking system comprising at least a camera to sense a movement of a second portion of the individual that is in view of the camera and a processor to predict a position of a first portion of the individual that is out of view of the three-dimensional tracking system based on the movement of the second portion of the individual;

tracking one or more objects in a work area using the three-dimensional tracking system comprising at least a sensor embedded in each of the one or more objects;

identifying, using the three-dimensional tracking system, an activity of the individual and any of the one or more objects that are affected by the activity;

determining, using an activity monitoring device comprising a computing device with a processor, whether the activity violates one or more procedural rules pertaining to one or more of the individual, the work area, and the one or more objects; and providing a notification of a violation to an output device.

2. The computer-readable storage medium of claim 1, wherein tracking the one or more objects comprises tracking a food item.

3. The computer-readable storage medium of claim 1, wherein tracking the one or more objects comprises tracking tableware.

4. The computer-readable storage medium of claim 1, wherein tracking the one or more objects comprises tracking a cleaning implement.

5. The computer-readable storage medium of claim 1, wherein tracking an individual and one or more objects in a work area comprises tracking the individual and the one or more objects in a kitchen.

6. The computer-readable storage medium of claim 1, wherein tracking comprises tracking an individual and one or more objects in a work area logically divided into two or more logical areas.

7. The computer-readable storage medium of claim 6, wherein the two or more logical areas comprise a raw meat area.

8. The computer-readable storage medium of claim 6, wherein the two or more logical areas comprise a hand washing area.

9. The computer-readable storage medium of claim 1, wherein the identified activity comprises contact between the individual and an object of the one or more objects.

10. The computer-readable storage medium of claim 1, wherein the identified activity comprises contact between an individual and a surface of the work area.

11. The computer-readable storage medium of claim 1, wherein the identified activity comprises contact between an object of the one or more objects and a surface of the work area.

12. The computer-readable storage medium of claim 1, wherein the identified activity comprises an activity having a risk of contaminating an object of the one or more objects.

13. The computer-readable storage medium of claim 1, wherein the identified activity comprises an activity having a risk of contaminating at least a portion of the work area.

14. The computer-readable storage medium of claim 1, wherein a procedural rule of the one or more procedural rules defines violation of a food handling procedure and determining comprises determining whether the activity violates the food handling procedure.

15. The computer-readable storage medium of claim 1, wherein the procedural rule defines a combination of one or more work area conditions that comprise a violation and wherein determining whether the activity violates the procedural rule comprises comparing current work area conditions to the defined combination of work area conditions.

16. The computer-readable storage medium of claim 1, wherein providing a notification comprises indicating in the work area an occurrence of a violation in response to determining that the activity violates a procedural rule of the one or more procedural rules.

17. The computer-readable storage medium of claim 16, wherein indicating comprises visually indicating the occurrence of the violation.

18. The computer-readable storage medium of claim 17, wherein visually indicating comprises spotlighting one or more of an object of the one or more objects, the individual, and a portion of the work area using a spotlight.

19. The computer-readable storage medium of claim 17, wherein visually indicating comprises displaying on a display a diagram of the work area indicating the occurrence of the violation.

20. The computer-readable storage medium of claim 16, wherein indicating comprises audibly playing a sound indicating the occurrence of the violation.

21. The computer-readable storage medium of claim 1, the method further comprising maintaining a history for the one or more objects, the individual, and portions of the work area.

22. The computer-readable storage medium of claim 21, wherein determining whether the activity violates a procedural rule is based on the history.

23. The computer-readable storage medium of claim 21, the method further comprising determining a contamination status of one or more of an object of the one or more objects, a portion of the work area, and the individual based on the history.

24. The computer-readable storage medium of claim 1, the method further comprising maintaining a database of violating activities and one or more work area conditions associated with each violating activity.

25. The computer-readable storage medium of claim 24, the method further comprising analyzing the database to identify a combination of the associated workplace conditions having a correlation to a violating activity.

26. The computer-readable storage medium of claim 24, the method further comprising analyzing the database to identify a procedure having a high correlation to a violating activity.

27. The computer-readable storage medium of claim 24, the method further comprising analyzing the database to identify a physical layout feature having a high correlation to a violating activity.

28. The computer-readable storage medium of claim 24, the method further comprising analyzing the database to identify an individual having a high correlation to a violating activity.

29. The computer-readable storage medium of claim 24, the method further comprising detecting a combination of the associated workplace conditions having a correlation to a violating activity and providing a warning.

30. A system for activity monitoring, the system comprising:

a tracking component to:
track an individual in a work area using a three-dimensional tracking system comprising at least a camera to sense a movement of a second portion of the individual that is in view of the camera and a processor to predict a position of a first portion of the individual that is out of view of the three-dimensional tracking system based on the movement of the second portion of the individual;

tracking one or more objects in a work area using the three-dimensional tracking system comprising at least a sensor embedded in each of the one or more objects;

an activity identification component to identify, using the three-dimensional tracking system, an activity of the individual and any of the one or more objects that are affected by the activity;

a procedural component comprising a computing device with a processor to determine whether the activity violates one or more procedural rules pertaining to one or more of the individual, the work area, and the one or more objects; and a notification component to provide a notification of a violation using a visual output within the work area.

31. The system of claim 30, further comprising a tracking storage component to store information regarding tracking of the individual and the one or more objects in the work area.

32. The system of claim 31, wherein the tracking storage component stores video footage of the work area.

33. The system of claim 32, wherein the tracking storage component stores video footage comprising video footage corresponding to a violation.

34. The system of claim 31, wherein the tracking storage component stores abstracted information regarding one or more of the work area, the activity of the individual, and the one or more objects.

35. The system of claim 30, wherein the three-dimensional tracking system comprises a tracer detection component to detect a tracer material, the tracer material comprising a material that transfers to a contacting surface in response to contact with the tracer material.

36. The system of claim 35, wherein the three-dimensional tracking system comprises a tracer trigger component to trigger detectability of the tracer material.

37. The system of claim 30, wherein the notification component provides the notification by automatically issuing a citation in response to the procedural component determining that the activity violates the one or more procedural rules.

38. The system of claim 37, wherein the citation indicates violation of a health violation.

39. A method for activity monitoring, the method comprising:

tracking an individual using a three-dimensional tracking system comprising at least a camera to sense a movement of a second portion of the individual that is in view of the camera and a processor to predict a position of a first portion of the individual that is out of view of the three-dimensional tracking system based on the movement of the second portion of the individual;

tracking one or more objects in a work area using the three-dimensional tracking system comprising at least a sensor embedded in each of the one or more objects;

identifying, using the three-dimensional tracking system, an activity of the individual and any of the one or more objects that are affected by the activity;

determining, using an activity monitoring device comprising a computing device with a processor, whether the activity violates one or more procedural rules pertaining to one or more of the individual, the work area, and the one or more objects; and providing a notification of a violation using a visual output within the work area.

\* \* \* \* \*